United States Patent
Refai et al.

(10) Patent No.: US 10,201,432 B2
(45) Date of Patent: Feb. 12, 2019

(54) VERTEBRAL BODY REPLACEMENT DEVICE AND METHOD FOR USE TO MAINTAIN A SPACE BETWEEN TWO VERTEBRAL BODIES WITHIN A SPINE

(71) Applicant: AESCULAP IMPLANT SYSTEMS, LLC, Center Valley, PA (US)

(72) Inventors: Daniel Refai, Atlanta, GA (US); Jeffrey A. Farris, Berne, IN (US); Jeffrey T. Ebersole, Columbia City, IN (US); Cory Alan Trischler, Fort Wayne, IN (US); Gordon Paul Kistler, Fort Wayne, IN (US); Charles Wing, Center Valley, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 879 days.

(21) Appl. No.: 14/222,862

(22) Filed: Mar. 24, 2014

(65) Prior Publication Data
US 2014/0222151 A1    Aug. 7, 2014

Related U.S. Application Data

(63) Continuation of application No. 13/900,782, filed on May 23, 2013, now Pat. No. 8,690,950, which is a
(Continued)

(51) Int. Cl.
*A61F 2/44* (2006.01)
*A61F 2/46* (2006.01)
(Continued)

(52) U.S. Cl.
CPC .............. *A61F 2/4465* (2013.01); *A61F 2/44* (2013.01); *A61F 2/4611* (2013.01);
(Continued)

(58) Field of Classification Search
USPC ............................................ 623/17.11–17.16
See application file for complete search history.

(56) References Cited

U.S. PATENT DOCUMENTS 2,333,033 A    10/1943  Mraz
4,157,715 A     6/1979  Westerhoff
(Continued)

FOREIGN PATENT DOCUMENTS

DE    3023942 A1    1/1982
DE    4012622 C1    7/1991
(Continued)

OTHER PUBLICATIONS

Japanese Application Serial No. 2010-531138, Japanese Office Action dated Jun. 15, 2012, 8 pgs.
(Continued)

*Primary Examiner* — Sameh Boles
(74) *Attorney, Agent, or Firm* — RatnerPrestia

(57) ABSTRACT

A vertebral body replacement device includes a body member and a central rod member having two threaded portions and configured to be operatively associated with the body member. The device also includes a first end member and a second end member with the end members configured to threadingly engage the threaded portions of the central rod member. The body member and the two end members are further constructed to inhibit rotational movement of the two end members when the device is positioned within a space within a spine as the two end members will engage the adjacent respective vertebral bodies following rotational actuation of the central rod member causing the end members to move in an axial direction relative to the body member, thereby allowing the two end members to apply a force to the two vertebral bodies. A surgical instrument and method for using the device are also disclosed.

20 Claims, 28 Drawing Sheets

Related U.S. Application Data continuation of application No. 13/475,279, filed on May 18, 2012, now Pat. No. 8,591,587, which is a continuation-in-part of application No. 11/928,532, filed on Oct. 30, 2007, now Pat. No. 8,182,537, and a continuation-in-part of application No. 13/312,486, filed on Dec. 6, 2011, now Pat. No. 8,702,719, which is a continuation of application No. 12/252,552, filed on Oct. 16, 2008, now Pat. No. 8,142,441.

(51) Int. Cl.
  *A61F 2/30* (2006.01)
  *A61F 2/28* (2006.01)

(52) U.S. Cl.
  CPC ........ *A61F 2/4637* (2013.01); *A61F 2/30734* (2013.01); *A61F 2/30744* (2013.01); *A61F 2/442* (2013.01); *A61F 2002/2835* (2013.01); *A61F 2002/3024* (2013.01); *A61F 2002/3052* (2013.01); *A61F 2002/3054* (2013.01); *A61F 2002/3055* (2013.01); *A61F 2002/30235* (2013.01); *A61F 2002/30331* (2013.01); *A61F 2002/30364* (2013.01); *A61F 2002/30367* (2013.01); *A61F 2002/30372* (2013.01); *A61F 2002/30405* (2013.01); *A61F 2002/30411* (2013.01); *A61F 2002/30433* (2013.01); *A61F 2002/30471* (2013.01); *A61F 2002/30492* (2013.01); *A61F 2002/30495* (2013.01); *A61F 2002/30507* (2013.01); *A61F 2002/30523* (2013.01); *A61F 2002/30525* (2013.01); *A61F 2002/30579* (2013.01); *A61F 2002/30601* (2013.01); *A61F 2002/30616* (2013.01); *A61F 2002/30772* (2013.01); *A61F 2002/30818* (2013.01); *A61F 2002/30841* (2013.01); *A61F 2002/30892* (2013.01); *A61F 2002/30904* (2013.01); *A61F 2002/4475* (2013.01); *A61F 2002/4622* (2013.01); *A61F 2002/4627* (2013.01); *A61F 2002/4628* (2013.01); *A61F 2002/4629* (2013.01); *A61F 2002/4638* (2013.01); *A61F 2002/4642* (2013.01)

(56) References Cited

U.S. PATENT DOCUMENTS

| | | |
|---|---|---|
| 4,289,123 A | 9/1981 | Dunn |
| 4,386,603 A | 6/1983 | Mayfield |
| 4,401,112 A | 8/1983 | Rezaian |
| 4,553,273 A | 11/1985 | Wu |
| 4,554,914 A | 11/1985 | Kapp |
| 4,599,086 A | 7/1986 | Doty |
| 4,636,217 A | 1/1987 | Ogilvie |
| 4,657,550 A | 4/1987 | Daher |
| 4,877,020 A | 10/1989 | Vich |
| 4,892,546 A | 1/1990 | Kotz |
| 4,932,975 A | 6/1990 | Main |
| 4,997,432 A | 3/1991 | Keller |
| 5,002,576 A | 3/1991 | Fuhrmann |
| 5,236,460 A | 8/1993 | Barber |
| 5,246,458 A | 9/1993 | Graham |
| 5,281,226 A | 1/1994 | Davydov |
| 5,290,312 A | 3/1994 | Kojimoto |
| 5,326,460 A | 7/1994 | Cheesman |
| 5,336,223 A | 8/1994 | Rogers |
| 5,344,459 A | 9/1994 | Swartz |
| 5,405,291 A | 4/1995 | Alcorn |
| 5,413,602 A | 5/1995 | Metz-stavenhagen |
| 5,443,514 A | 8/1995 | Steffee |
| 5,458,641 A | 10/1995 | Jimenez |
| 5,480,442 A | 1/1996 | Bertagnoli |
| 5,540,391 A | 7/1996 | Anderson |
| 5,571,190 A | 11/1996 | Ulrich |
| 5,571,192 A | 11/1996 | Schonhoffer |
| 5,658,335 A | 8/1997 | Allen |
| 5,702,453 A | 12/1997 | Rabbe |
| 5,702,455 A | 12/1997 | Saggar |
| 5,716,415 A | 2/1998 | Steffee |
| 5,723,013 A | 3/1998 | Jeanson |
| 5,776,197 A | 7/1998 | Rabbe |
| 5,776,198 A | 7/1998 | Rabbe |
| 5,800,547 A | 9/1998 | Schafer |
| 5,888,223 A | 3/1999 | Bray |
| 5,916,267 A | 6/1999 | Tienboon |
| 5,916,627 A | 6/1999 | Lessner |
| 5,989,290 A | 11/1999 | Biedermann |
| 6,015,436 A | 1/2000 | Schonhoffer |
| 6,045,579 A | 4/2000 | Hochshuler |
| 6,080,193 A | 6/2000 | Hochshuler |
| 6,106,557 A | 8/2000 | Robioneck |
| 6,113,605 A | 9/2000 | Storer |
| 6,126,660 A | 10/2000 | Dietz |
| 6,126,674 A | 10/2000 | Janzen |
| 6,129,763 A | 10/2000 | Chauvin |
| 6,159,215 A | 12/2000 | Urbahns |
| 6,176,881 B1 | 1/2001 | Schar |
| 6,190,143 B1 | 2/2001 | Jacobson |
| 6,190,414 B1 | 2/2001 | Young |
| 6,193,755 B1 | 2/2001 | Metz-stavenhagen |
| 6,193,756 B1 | 2/2001 | Studer |
| 6,200,348 B1 | 3/2001 | Biedermann |
| 6,214,050 B1 | 4/2001 | Huene |
| 6,296,665 B1 | 10/2001 | Strnad |
| 6,299,644 B1 | 10/2001 | Vanderschot |
| 6,319,257 B1 | 11/2001 | Carignan |
| 6,344,057 B1 | 2/2002 | Rabbe |
| 6,352,556 B1 | 3/2002 | Kretschmer |
| 6,375,382 B1 | 4/2002 | Clavat |
| 6,375,682 B1 | 4/2002 | Fleischmann |
| 6,375,683 B1 | 4/2002 | Crozet |
| 6,395,032 B1 | 5/2002 | Gauchet |
| 6,395,034 B1 | 5/2002 | Suddaby |
| 6,454,806 B1 | 9/2002 | Cohen |
| 6,478,800 B1 | 11/2002 | Fraser |
| 6,524,341 B2 | 2/2003 | Lang |
| 6,562,074 B2 | 5/2003 | Gerbec |
| 6,610,090 B1 | 8/2003 | Bohm |
| 6,616,695 B1 | 9/2003 | Crozet |
| 6,648,917 B2 | 11/2003 | Gerbec |
| 6,660,038 B2 | 12/2003 | Boyer |
| 6,699,246 B2 | 3/2004 | Zucherman |
| 6,719,796 B2 | 4/2004 | Cohen |
| 6,723,126 B1 | 4/2004 | Berry |
| 6,730,088 B2 | 5/2004 | Yeh |
| 6,752,832 B2 | 6/2004 | Neumann |
| 6,783,547 B2 | 8/2004 | Castro |
| 6,808,538 B2 | 10/2004 | Paponneau |
| 6,821,298 B1 | 11/2004 | Jackson |
| 6,835,206 B2 | 12/2004 | Jackson |
| 6,835,207 B2 | 12/2004 | Zacouto |
| 6,852,129 B2 | 2/2005 | Gerbec |
| 6,863,673 B2 | 3/2005 | Gerbec |
| 6,866,682 B1 | 3/2005 | An |
| 6,902,579 B2 | 6/2005 | Harms |
| 6,908,485 B2 | 6/2005 | Crozet |
| 6,953,477 B2 | 10/2005 | Berry |
| 6,981,989 B1 | 1/2006 | Fleischmann |
| 7,022,138 B2 | 4/2006 | Mashburn |
| 7,029,498 B2 | 4/2006 | Boehm |
| 7,056,343 B2 | 6/2006 | Schafer |
| 7,156,874 B2 | 1/2007 | Paponneau |
| 7,252,673 B2 | 8/2007 | Lim |
| 7,338,526 B2 | 3/2008 | Steinberg |
| 7,384,431 B2 | 6/2008 | Berry |
| 7,575,601 B2 | 8/2009 | Dickson |
| 7,588,573 B2 | 9/2009 | Berry |
| 7,621,953 B2 | 11/2009 | Braddock |
| 7,674,296 B2 | 3/2010 | Rhoda |
| 7,725,673 B2 | 5/2010 | Ishida |
| 7,819,922 B2 | 10/2010 | Sweeney |
| 7,918,888 B2 | 4/2011 | Hamada |

(56) References Cited

U.S. PATENT DOCUMENTS

| | | |
|---|---|---|
| 8,182,016 B2 | 5/2012 | Kaip et al. |
| 8,377,140 B2 | 2/2013 | DeFalco |
| 8,702,719 B2 | 4/2014 | Refai et al. |
| 2001/0005796 A1 | 6/2001 | Zdeblick |
| 2001/0014826 A1* | 8/2001 | Biedermann et al. ...... 623/17.11 |
| 2002/0068978 A1 | 6/2002 | Camino |
| 2002/0082695 A1 | 6/2002 | Neumann |
| 2002/0099443 A1 | 7/2002 | Messerli |
| 2002/0161441 A1 | 10/2002 | Lang |
| 2003/0045877 A1 | 3/2003 | Yeh |
| 2003/0045887 A1 | 3/2003 | Sakurai |
| 2003/0083747 A1 | 5/2003 | Winterbottom |
| 2003/0191531 A1 | 10/2003 | Berry |
| 2004/0049271 A1 | 3/2004 | Biedermann |
| 2004/0059271 A1 | 3/2004 | Berry |
| 2004/0093083 A1 | 5/2004 | Branch |
| 2004/0133280 A1 | 7/2004 | Trieu |
| 2004/0153160 A1 | 8/2004 | Carrasco |
| 2004/0172129 A1 | 9/2004 | Schafer |
| 2004/0181283 A1 | 9/2004 | Boyer |
| 2004/0186569 A1 | 9/2004 | Berry |
| 2004/0186576 A1 | 9/2004 | Biscup |
| 2004/0210312 A1 | 10/2004 | Neumann |
| 2005/0004572 A1 | 1/2005 | Biedermann |
| 2005/0058879 A1 | 3/2005 | Guay |
| 2005/0060036 A1 | 3/2005 | Schultz |
| 2005/0085910 A1 | 4/2005 | Sweeney |
| 2005/0090898 A1 | 4/2005 | Berry |
| 2005/0113921 A1 | 5/2005 | An |
| 2005/0143749 A1 | 6/2005 | Zalenski |
| 2005/0159814 A1 | 7/2005 | Karahalios |
| 2005/0187634 A1 | 8/2005 | Berry |
| 2005/0216084 A1* | 9/2005 | Fleischmann et al. ..... 623/17.11 |
| 2005/0234550 A1 | 10/2005 | Metz-stavenhagen |
| 2006/0004376 A1 | 1/2006 | Shipp |
| 2006/0004447 A1 | 1/2006 | Mastrorio |
| 2006/0058877 A1* | 3/2006 | Gutlin et al. .............. 623/17.11 |
| 2006/0058879 A1 | 3/2006 | Metz-stavenhagen |
| 2006/0074488 A1 | 4/2006 | Abdou |
| 2006/0074490 A1 | 4/2006 | Sweeney |
| 2006/0085073 A1 | 4/2006 | Raiszadeh |
| 2006/0100710 A1 | 5/2006 | Gutlin |
| 2006/0142859 A1 | 6/2006 | McLuen |
| 2006/0149371 A1 | 7/2006 | Marik |
| 2006/0200244 A1 | 9/2006 | Assaker |
| 2006/0224241 A1 | 10/2006 | Butler |
| 2006/0235521 A1 | 10/2006 | Zucherman |
| 2006/0241762 A1 | 10/2006 | Kraus |
| 2006/0241770 A1 | 10/2006 | Rhoda |
| 2006/0293755 A1 | 12/2006 | Lindner |
| 2007/0093901 A1 | 4/2007 | Grotz |
| 2007/0129805 A1 | 6/2007 | Braddock |
| 2007/0173855 A1 | 7/2007 | Winn |
| 2007/0191954 A1 | 8/2007 | Hansell |
| 2007/0203490 A1 | 8/2007 | Zucherman |
| 2007/0233254 A1 | 10/2007 | Grotz |
| 2007/0250171 A1 | 10/2007 | Bonin |
| 2007/0255407 A1 | 11/2007 | Castleman |
| 2007/0255408 A1 | 11/2007 | Castleman |
| 2007/0255410 A1 | 11/2007 | Dickson |
| 2007/0255413 A1 | 11/2007 | Edie |
| 2007/0255421 A1 | 11/2007 | Dickson |
| 2008/0004705 A1 | 1/2008 | Rogeau |
| 2008/0021555 A1 | 1/2008 | White |
| 2008/0021556 A1 | 1/2008 | Edie |
| 2008/0051896 A1 | 2/2008 | Suddaby |
| 2008/0058931 A1 | 3/2008 | White |
| 2008/0140207 A1 | 6/2008 | Olmos |
| 2008/0154305 A1 | 6/2008 | Foley |
| 2008/0167726 A1 | 7/2008 | Melkent |
| 2008/0243254 A1 | 10/2008 | Butler |
| 2008/0255574 A1 | 10/2008 | Dye |
| 2008/0287957 A1 | 11/2008 | Hester |
| 2008/0288073 A1 | 11/2008 | Renganath |
| 2009/0030421 A1 | 1/2009 | Hawkins |
| 2009/0076610 A1 | 3/2009 | Afzai |
| 2009/0105832 A1 | 4/2009 | Allain |
| 2009/0112220 A1 | 4/2009 | Kraus |
| 2009/0112324 A1 | 4/2009 | Refai |
| 2009/0112325 A1 | 4/2009 | Refai |
| 2009/0216331 A1 | 8/2009 | Grotz |
| 2010/0211119 A1 | 8/2010 | Refai |
| 2011/0087328 A1 | 4/2011 | Dickson |

FOREIGN PATENT DOCUMENTS

| | | |
|---|---|---|
| DE | 9107494 | 9/1991 |
| DE | 4109941 A1 | 10/1992 |
| DE | 4409392 A1 | 9/1995 |
| DE | 4423257 A1 | 1/1996 |
| DE | 19500170 C1 | 2/1996 |
| DE | 19509317 A1 | 9/1996 |
| DE | 19519101 A1 | 11/1996 |
| DE | 19622827 A1 | 12/1997 |
| DE | 29616778 U1 | 1/1998 |
| DE | 3729600 A1 | 3/1999 |
| DE | 19804765 A1 | 8/1999 |
| DE | 20213013 U1 | 12/2002 |
| DE | 20320974 U1 | 8/2005 |
| DE | 10357926 B3 | 9/2005 |
| DE | 202008001261 U1 | 4/2008 |
| EP | 0188954 A1 | 7/1986 |
| EP | 0290767 A1 | 11/1988 |
| EP | 0490159 A1 | 6/1992 |
| EP | 0567424 A1 | 10/1993 |
| EP | 0832622 A2 | 4/1998 |
| EP | 0968692 A1 | 1/2000 |
| EP | 1080703 A2 | 3/2001 |
| EP | 1188424 A1 | 3/2002 |
| EP | 1219266 A1 | 7/2002 |
| EP | 1459710 A2 | 9/2004 |
| EP | 1491165 A1 | 12/2004 |
| EP | 1867304 A1 | 12/2007 |
| FR | 2916956 | 12/2008 |
| JP | 62164458 A | 7/1987 |
| JP | 2011502005 A | 1/2011 |
| JP | 2012505714 A | 3/2012 |
| SU | 1560184 A1 | 4/1990 |
| SU | 1739989 A1 | 6/1992 |
| WO | 9201428 A1 | 2/1992 |
| WO | 9418913 A1 | 9/1994 |
| WO | 9525486 A1 | 9/1995 |
| WO | 9617564 A1 | 6/1996 |
| WO | 9637170 A1 | 11/1996 |
| WO | 9747258 A1 | 12/1997 |
| WO | 9846173 A1 | 10/1998 |
| WO | 9939665 A1 | 8/1999 |
| WO | 9956675 A1 | 11/1999 |
| WO | 9963913 A2 | 12/1999 |
| WO | 0023013 | 4/2000 |
| WO | 03096937 | 11/2003 |
| WO | 2004019827 A1 | 3/2004 |
| WO | 2004026157 A2 | 4/2004 |
| WO | 2004052245 A1 | 6/2004 |
| WO | 2004093751 A2 | 11/2004 |
| WO | 2004096103 A1 | 11/2004 |
| WO | 2004100837 A1 | 11/2004 |
| WO | 2005055887 A2 | 6/2005 |
| WO | 2006065910 A1 | 6/2006 |
| WO | 2007076261 A1 | 7/2007 |
| WO | 2008065450 A1 | 6/2008 |
| WO | 2008099277 | 8/2008 |
| WO | 2009058576 A1 | 5/2009 |
| WO | 2010045301 | 4/2010 |

OTHER PUBLICATIONS

Patent Examination report No. 1 received in Australian Patent Application No. 2008319067, dated Dec. 14, 2012.
International Search Report and Written Opinion issued in related International Application No. PCT/US2013/041524, dated Aug. 22, 2013.

(56) References Cited

OTHER PUBLICATIONS

U.S. Appl. No. 13/475,279, Non Final Office Action dated Apr. 8, 2013.
U.S. Appl. No. 13/900,782, Notice of Allowance dated Nov. 7, 2013.
U.S. Appl. No. 13/475,279, Notice of Allowance dated Sep. 27, 2013.
U.S. Appl. No. 11/928,553, Final Office Action dated Feb. 15, 2013.
European Official Action for Application No. 08 846 136.3 dated May 22, 2012.
U.S. Appl. No. 11/628,532, Office Action dated Jul. 21, 2011.
U.S. Appl. No. 11/928,532, Notice of Allowance dated Jan. 20, 2012.
Japanese Office Action for Japanese Application No. 2015-512876, dated Feb. 13, 2017 with translation, 5 pages.
U.S. Appl. No. 11/928,553, Final Office Action dated Mar. 17, 2011.
U.S. Appl. No. 11/928,553, Non Final Office Action dated Jul. 31, 2012.
U.S. Appl. No. 12/252,552, Non Final Office Action dated Sep. 6, 2011, 6 pages.
U.S. Appl. No. 11/928,553, Non Final Office Action dated Dec. 7, 2010, 30 pgs.
U.S. Appl. No. 12/388,581, Office Action dated Aug. 26, 2011.
U.S. Appl. No. 12/252,552, Notice of Allowance dated Dec. 13, 2011, 12 pgs.
International Application Serial No. PCT/US2008/080143, International Search Report and Written Opinion dated Feb. 24, 2009, 14 pgs.
International Application Serial No. PCT/US2009/060608, International Search Report and Written Opinion dated Feb. 17, 2010, 17 pgs.
International Application Serial No. PCT/US2008/080127, International Search Report and Written Opinion dated Feb. 23, 2009, 17 pgs.
International Application Serial No. PCT/US2010/022805, International Search report and Written Opinion dated Jun. 24, 2010.

\* cited by examiner

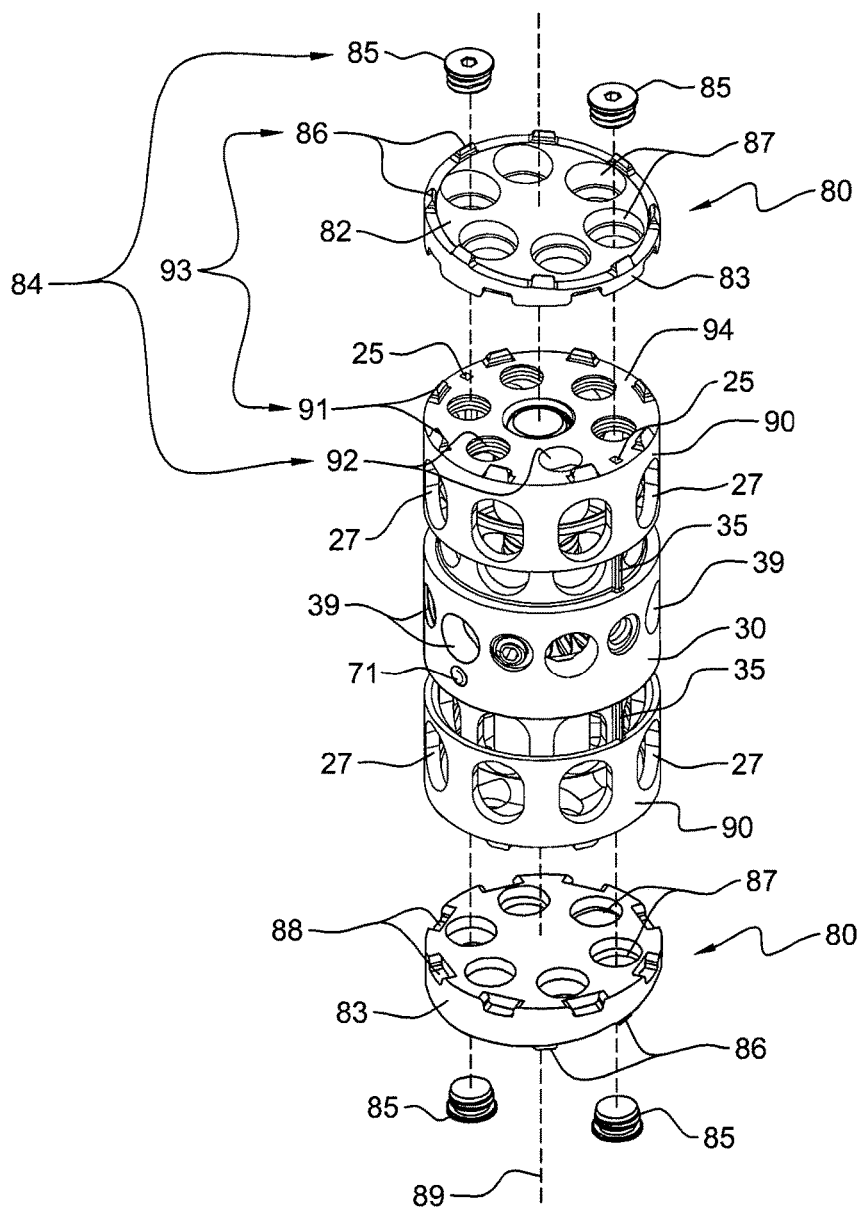
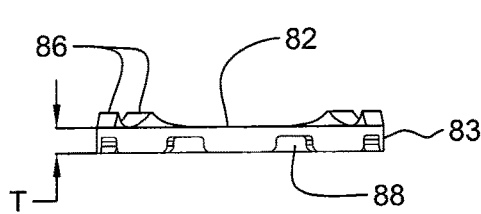
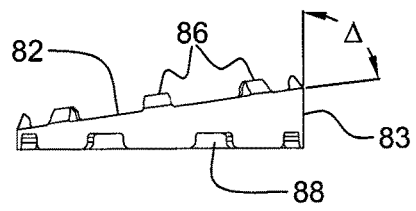
FIG. 9
FIG. 10A  FIG. 10B

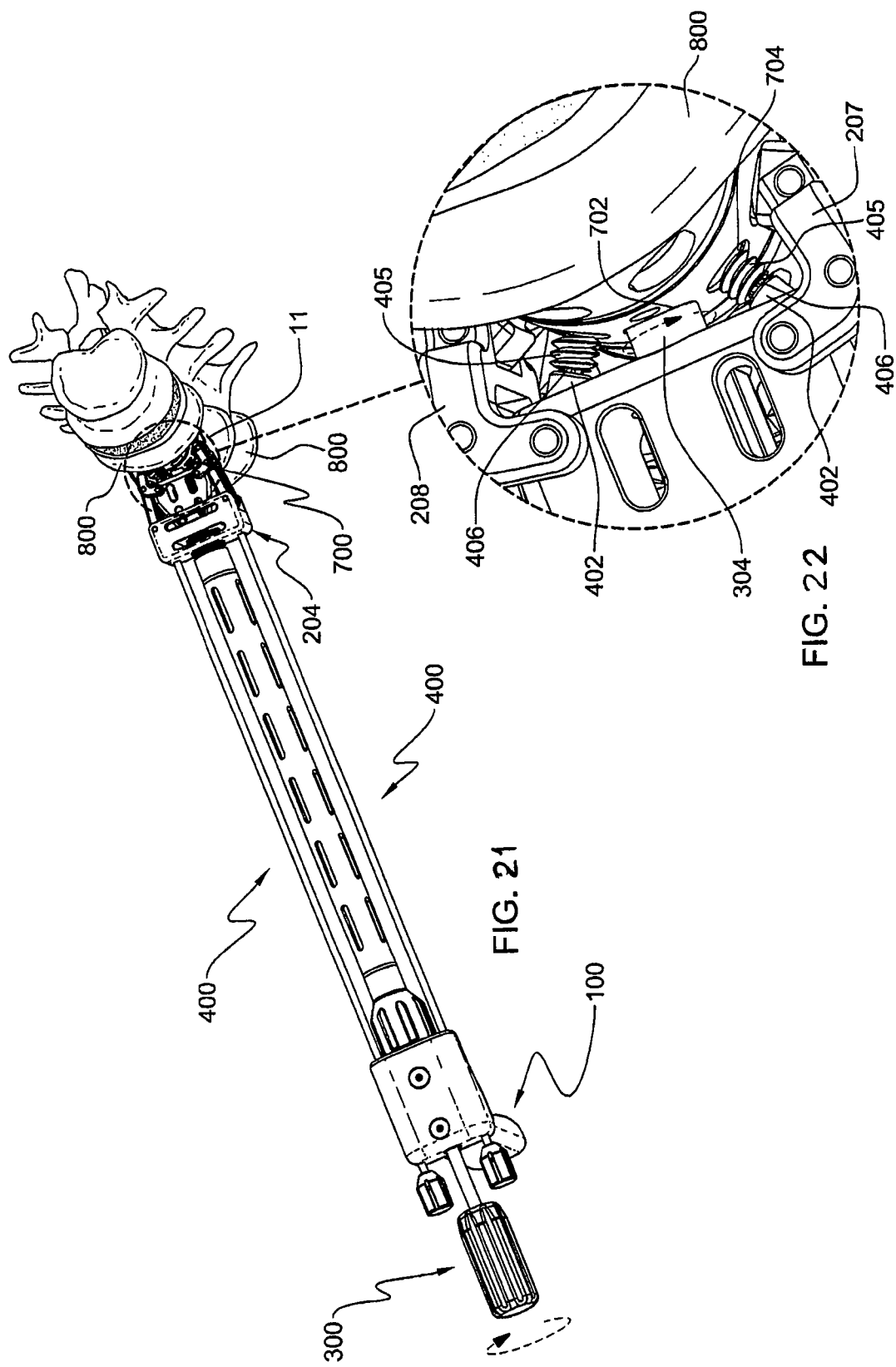

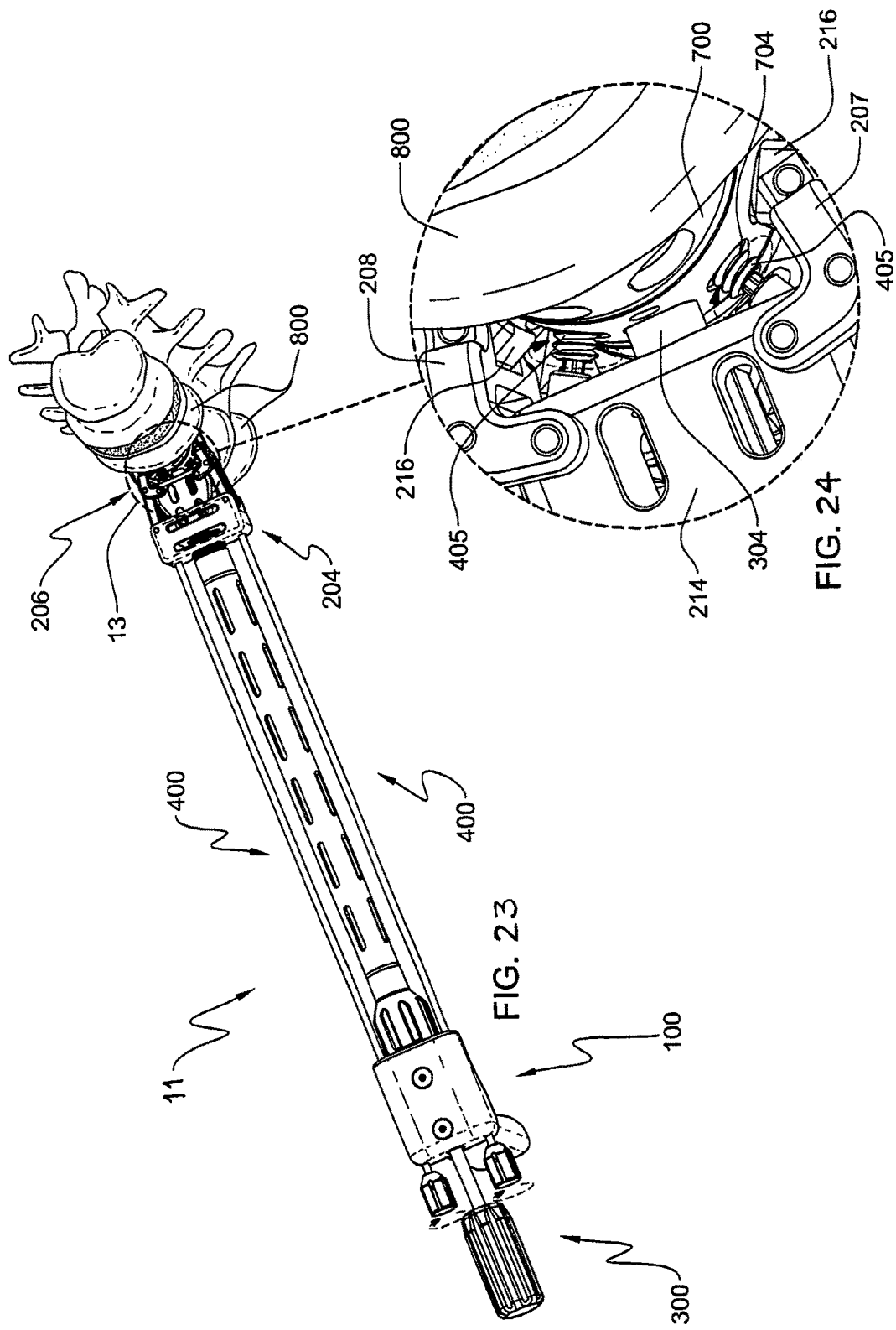

VERTEBRAL BODY REPLACEMENT DEVICE AND METHOD FOR USE TO MAINTAIN A SPACE BETWEEN TWO VERTEBRAL BODIES WITHIN A SPINE

CROSS-REFERENCE TO RELATED APPLICATIONS

This application is a continuation of U.S. application Ser. No. 13/900,782, filed May 23, 2013, which is a continuation of U.S. application Ser. No. 13/475,279, filed May 18, 2012, and now issued as U.S. Pat. No. 8,591,587, which is a continuation-in-part of U.S. application Ser. No. 11/928,532, filed Oct. 30, 2007 and now issued as U.S. Pat. No. 8,182,537, and a continuation-in-part of U.S. application Ser. No. 13/312,486, filed Dec. 6, 2011, which is a continuation of U.S. application Ser. No. 12/252,552, filed Oct. 16, 2008 and now issued as U.S. Pat. No. 8,142,441. The contents of all of the foregoing applications and issued patents are incorporated by reference herein in their entireties and for all purposes.

TECHNICAL FIELD

The present invention relates generally to orthopaedic and neurosurgical implants used for insertion within the spine, and more specifically, but not exclusively, concerns devices implanted within the spinal column to replace a resected, fractured or diseased vertebral body and to maintain or reestablish proper spacing between the remaining adjacent vertebral bodies.

BACKGROUND

Damage or disease that affects the integral structure of a vertebral body within an individual's spinal column may lead to neurologic impairment with possible permanent damage to the spinal cord as well as improper neck and back alignment. Maintaining anatomic spacing within the spinal column is critical to ensuring continued functionality of the spinal cord and nerve roots and avoidance of long term serious neurological impairment.

Typically, spinal implants that are used as a spacer type of device have a fixed overall length and are implanted without the ability to adjust the degree of expansion or curvature. Recent developments of spinal spacers have resulted in devices that may be lengthened in vivo by rotary motion to match the space presented by the missing vertebral body. In use, these spinal spacers can be expanded until the height of the spacer reaches the height of the disc space in which the spacer is inserted. Problems that have been seen with these types of designs include post-placement migration attributable to the forces applied to the implant during use risking the patient to neurologic injury. The proper sizing of the implant relative to the presented clinical space and the achievement of optimum expansion are important to ensure that the implant fills the space and does not loosen or migrate post implantation. To achieve the required distraction, it is important that the implant insertion and distraction instrument provides the user with optimum handling characteristics. Suitable device access ports for height manipulation are very important, as are a good assortment of endplate angulation possibilities.

Spacers that are lengthened by rotary motion may include gear mechanisms that are engaged by and rotated by a driver tool. For some of these spacers, surgeons rely at least in part on tactile feel to determine when the spacer is fully expanded; i.e. when the ends of the spacer contact the vertebrae on either side of the disc space. In an ideal operation, the gear mechanism rotates with very little resistance until the ends of the implant contact the adjacent vertebrae. Once contact occurs, the device exhibits resistance to further expansion, and that resistance can be sensed by the surgeon as a signal that the implant is fully expanded in the disc space. If the gear mechanism does not rotate properly, due to improper engagement with the driver tool, damaged gear teeth, or other reason, then the surgeon may sense resistance from the implant before the implant is completely expanded, referred to herein as "premature resistance". Premature resistance can make it difficult or impossible for the surgeon to sense precisely when the implant is fully expanded in contact with the adjacent vertebrae. In some cases, premature resistance from the implant can be mistaken as a signal that that the implant is completely expanded, when in fact it is not.

SUMMARY

The drawbacks of known vertebral body replacement devices are addressed in many respects by vertebral body replacement devices in accordance with the invention.

In one embodiment, a vertebral body replacement device may include a body member having an outer wall for engagement with a tool. The outer wall may include a plurality of tool ports arranged along at least a portion of a perimeter of the body member. The vertebral body replacement device may also include a central rod member configured to be operatively associated within the body member. The central rod member may have a first threaded portion, a second threaded portion, and a gear wheel portion. The gear wheel portion may include a toothed surface and a support surface. The vertebral body replacement device may further include a first end member and a second end member. The first end member may be configured to threadingly engage the first threaded portion of the central rod member, and the second end member may be configured to threadingly engage the second threaded portion of the central rod member.

The body member, first end member and second end member may be configured to inhibit rotational movement of the first and second end members when the vertebral body replacement device is disposed within a space within a spinal column with the first and second end members engaging respective vertebral bodies of the spinal column and the central rod member is rotationally actuated to move the first end member and the second end member in an axial direction relative to the body member allowing for the first end member and the second end member to apply a force to the two vertebral bodies to maintain a desired space therebetween.

The plurality of tool ports may include a first tool port, a second tool port and a third tool port. The third tool port may be positioned between the first and second tool ports, with the toothed surface of the gear wheel portion exposed through the third tool port when the central rod member is operatively associated within the body member. In addition, the third tool port may be configured to receive a tool that engages the gear wheel portion.

The first tool port and the second tool port may collectively form an alignment and indexing mechanism that allows a tool to be inserted through the third tool port and into proper engagement with the gear wheel portion. The first tool port and second tool port may each comprise an elongated slot. The first tool port and second tool port may be equidistant from the first end member and the second end member.

The vertebral body replacement device may include a fourth tool port located in a position that is either superior to or inferior to the third tool port. A locking screw may be housed inside the fourth tool port. The locking screw may include an outer thread and the fourth tool port may include an inner thread in engagement with the outer thread. The inner thread may terminate at a point within the fourth tool port that is recessed inside and spaced from the outer wall to prevent the locking screw from being removed from the tool port through the outer wall.

The vertebral body replacement device may also include a fifth tool port. The fourth tool port may be located in a position that is superior to the third tool port, and the fifth tool port may be located in a position that is inferior to the third tool port.

The vertebral body replacement device may further include a support ring. The support ring may include a bearing surface contacting the central rod member when the central rod member is operatively positioned within the body member. The support surface of the gear wheel portion may be configured to contact the bearing surface of the support ring when the central rod member is operatively positioned within the body member.

The central rod member may include a central axis extending between the first threaded portion and the second threaded portion thereof. A rotational axis of the gear wheel portion is substantially coaxial to the central axis of the central rod member. When the gear wheel portion is rotated about the rotational axis, the first and second threaded portions may correspondingly rotate about the central axis of the central rod member.

The vertebral body replacement device may also include at least one footplate member. The at least one footplate member may couple to at least one of the first end member and the second end member. The first end member and the second end member may each include an external wall, an internal wall and an end wall. The first end member and the second end member may also each include at least one travel limiting mechanism that engages the body member to limit movement of the first end member and second end member relative to the body member. The at least one travel limiting mechanism may include a pin configured to slidingly engage the body member.

At least one of the first end member and the second end member may feature at least one projection that is disposed on the end wall and extends in an outward direction. The first end member and the second end member may each comprise at least one hole disposed in at least one of the external wall and the end wall and extending therethrough, thereby allowing for the placement of bio-compatible material within the first and second end members. The body member may include an inner wall and at least one hole extending from the outer wall through the inner wall therethrough, thereby allowing for the placement of bio-compatible material within the body member.

The vertebral body replacement device may further include at least one footplate member and a snap ring. The snap ring may detachably couple the at least one footplate member at least one of the first end member and the second end member.

Additional features and advantages are realized through the techniques of the present invention. Other embodiments and aspects of the invention are described in detail herein and are considered a part of the claimed invention.

BRIEF DESCRIPTION OF THE DRAWINGS

The foregoing summary and the detailed description that follows will be better understood in conjunction with the accompanying drawing figures, of which:

FIG. 9 is a perspective view of an alternative embodiment of a vertebral body replacement device, with a superiorly positioned, detachable footplate member and an inferiorly positioned, detachable footplate member shown prior to being coupled to the superiorly positioned end member and an inferiorly positioned end member, respectively, in accordance with an aspect of the present invention;

FIG. 10A is a side elevational view of a detachable footplate member of the vertebral body replacement device of FIG. 9, showing an end surface being oriented normal relative to a sidewall, in accordance with an aspect of the present invention;

FIG. 10B is a side elevational view of an alternative embodiment of a detachable footplate member used with the vertebral body replacement device of FIG. 9, showing the end surface being oriented at an angle relative to the sidewall, in accordance with an aspect of the present invention;

FIG. 21 is a perspective view of the spinal implant coupled to the surgical instrument of FIG. 12, shown positioned in a space between two vertebral bodies with the length control mechanism being rotated to extend the spinal implant to allow the ends to make contact with the superior and inferior vertebral bodies to maintain a desired spacing arrangement within a spinal column, in accordance with an aspect of the present invention;

FIG. 22 is an enlarged top view of distal end of the surgical instrument of FIG. 12, showing the gear assembly inserted into the spinal implant, in accordance with an aspect of the present invention;

FIG. 23 is a perspective view of the spinal implant coupled to the surgical instrument of FIG. 12, shown positioned in a space between two vertebral bodies following final length determination with the locking mechanism being rotated, in accordance with an aspect of the present invention;

FIG. 24 is an enlarged top view of the distal end of the surgical instrument of FIG. 12, showing the coupling end and attached locking pin/screw being inserted into the spinal implant, in accordance with an aspect of the present invention;

DETAILED DESCRIPTION OF EMBODIMENTS

Generally stated, disclosed herein is a vertebral body replacement device or vertebral spacer that typically includes a body member, a central rod member, a support ring, two end members and at least one footplate member. As used herein, the terms "vertebral body replacement device"

and "vertebral spacer" may be used interchangeably as they essentially describe the same type of implant device. Further, described herein is a surgical method for using the vertebral body replacement device to maintain a space between two vertebral bodies within a patient suffering from a diseased or damaged spinal column.

Figure 1:
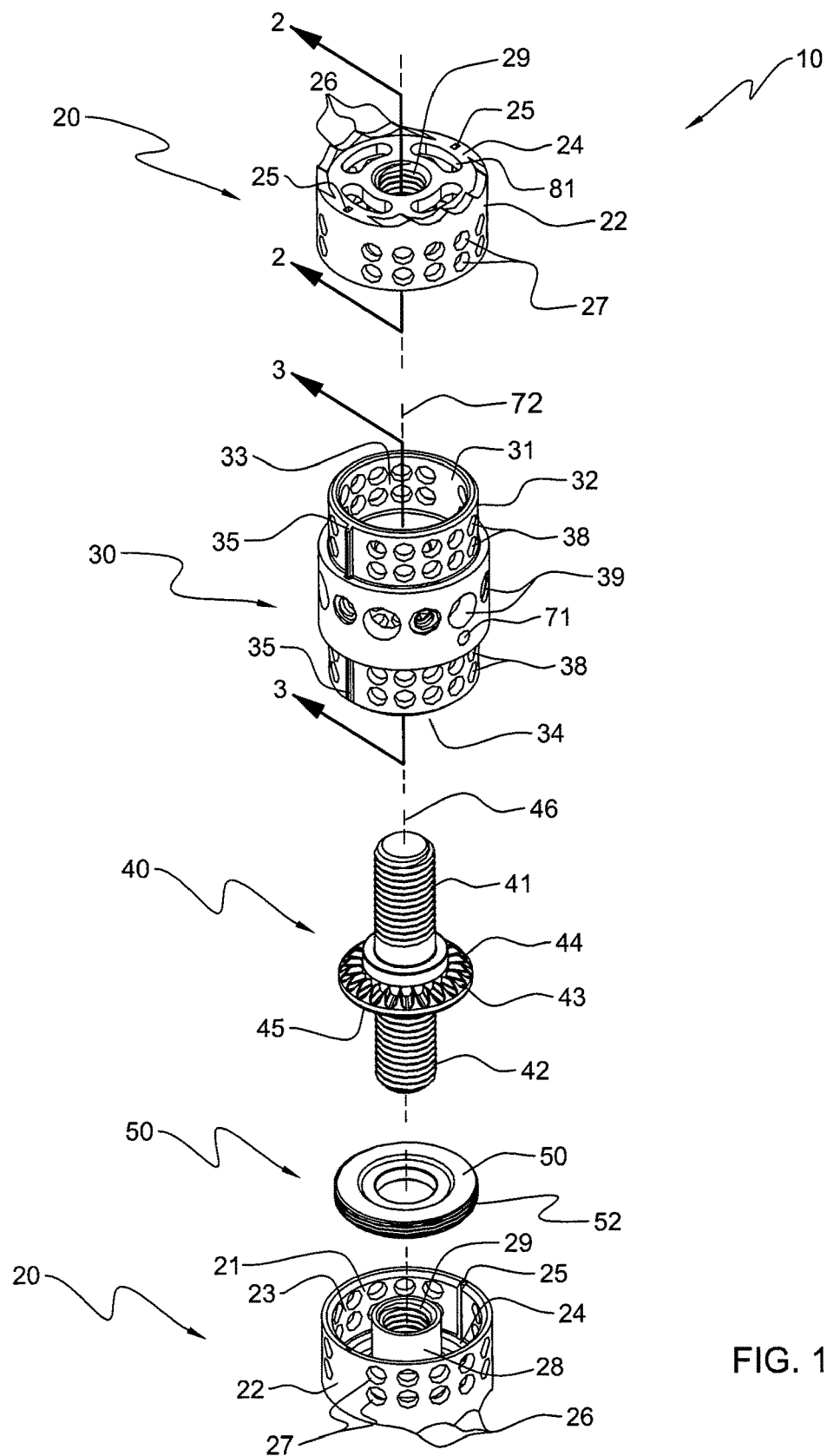
FIG. 1 is a perspective, exploded view of one embodiment of a vertebral body replacement device, in accordance with an aspect of the present invention.

As depicted in FIG. 1, the general arrangement of a vertebral body replacement device 10, in accordance with an aspect of the present invention, includes a body member 30, at least two end members 20, a central rod member 40 and a support ring 50. In this detailed description and the following claims, the words proximal, distal, anterior, posterior, medial, lateral, superior and inferior are defined by their standard usage for indicating a particular part of a bone or prosthesis according to the relative disposition of the natural bone or directional terms of reference. For example, "proximal" means the portion of a prosthesis nearest the torso, while "distal" indicates the portion of the prosthesis farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

With reference to FIG. 1, vertebral body replacement device 10 includes body member 30, at least two end members 20 positioned superior and inferior relative to body member 30, a central rod member 40 for placement within body member 30 and support ring 50 that is configured to contact and secure central rod member 40 within body member 30.

Exhibited in FIG. 1, body member 30 also includes an inner wall 31 and an outer wall 32, at least one hole 38 extending from outer wall 32 through inner wall 31. Further, body member 30 has at least one anti-rotational rib 35 disposed on and extending for substantially the entire length of outer wall 32. At least one rib 35 is oriented in a superior to inferior direction relative to body member 30 and substantially parallel to a longitudinal axis 72 of body member 30. At least one hole 38 is used for the placement of bone graft or other biocompatible material that will facilitate bone fusion to occur in vivo following implantation of the device. It should be understood to those skilled in the art that body member 30 may be available to the operating surgeon in various outside diameter sizes and longitudinal lengths L (see FIG. 3). Having multiple sized body members 30 as part of an implant system allows the operating surgeon to use vertebral body replacement device 10 in various levels or segments of the spine (i.e., smaller sizes in the cervical spine, medium sizes in the thoracic spine and larger sizes in the lumbar spine).

Figure 3:
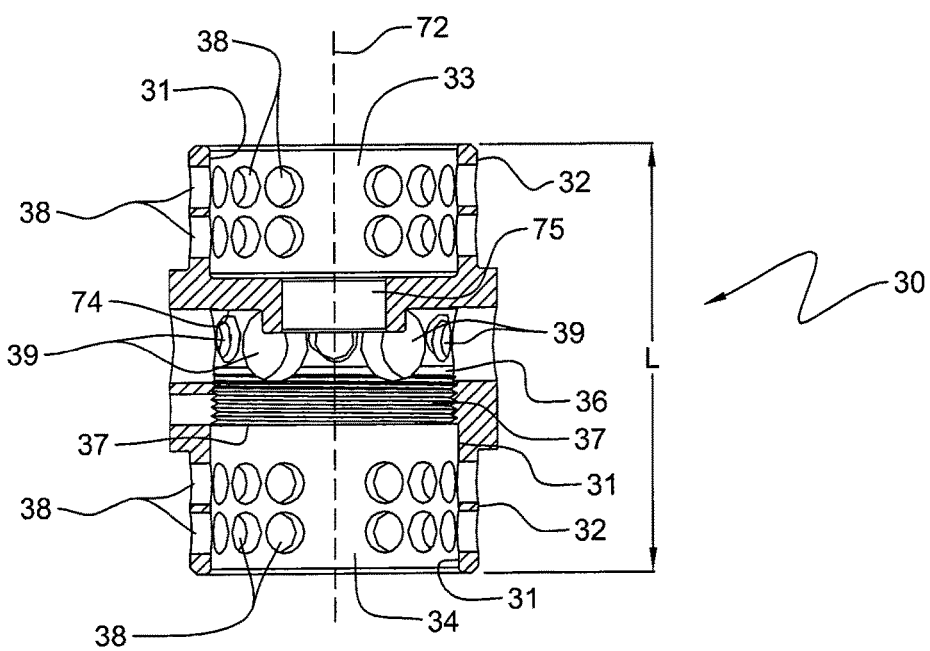
FIG. 3 is a cross-sectional, side elevational view of a body member of the vertebral body replacement device of FIG. 1 taken along line 3-3, showing two receptacle ends and internal threads for engaging a support ring, in accordance with an aspect of the present invention.

As shown in the cross-sectional view of FIG. 3, body member 30 further includes a first or superiorly positioned end receptacle 33 and a second or inferiorly positioned end receptacle 34 with longitudinal axis 72 extending between these two structures within elongate body member 30. A middle chamber 36 is defined by inner wall 31 and is bound superiorly by first end receptacle 33 and inferiorly by second end receptacle 34. At least one tool port hole 39 extends into middle chamber 36 through outer wall 32 and inner wall 31. In addition, inner wall 31 of middle chamber 36 includes a set of internal threads 37 positioned in the bottom portion of middle chamber 36. Internal threads are sized and configured to threadingly engage the external threads 52 of support ring 50 (not shown). A ceiling surface 74 bounds the superior portion of middle chamber 36 with a centralized opening 75 positioned through ceiling surface 74. Although not shown, when vertebral body replacement device 10 is fully assembled and in use, central rod member 40 is operatively associated with body member 30 by being configured to allow for a superior threaded portion 41 of central rod member 40 to pass through centralized opening 75 resulting in a collar element 47 of central rod member 40 contacting ceiling surface 74. Following placement of superior threaded portion 41 of central rod member 40 through centralized opening 75, central rod member 40 is moveably secured within middle chamber 36 by threadingly coupling support ring 50 to internal threads 37 of middle chamber 36 resulting in a bearing surface 51 of support ring 50 making pressing contact with a support surface 45 of central rod member 40. Body member 30 further includes at least one locking pin hole 71 (as seen in FIG. 1) that passes through outer wall 32 and inner wall 31 into middle chamber 36. Although not shown, following final placement and adjustment of assembled vertebral body replacement device 10, a corresponding threaded pin or bolt may screw into at least one locking pin hole 71 resulting in central rod member 40 being secured in position, fixing the overall length of vertebral body replacement 10.

Figure 4:
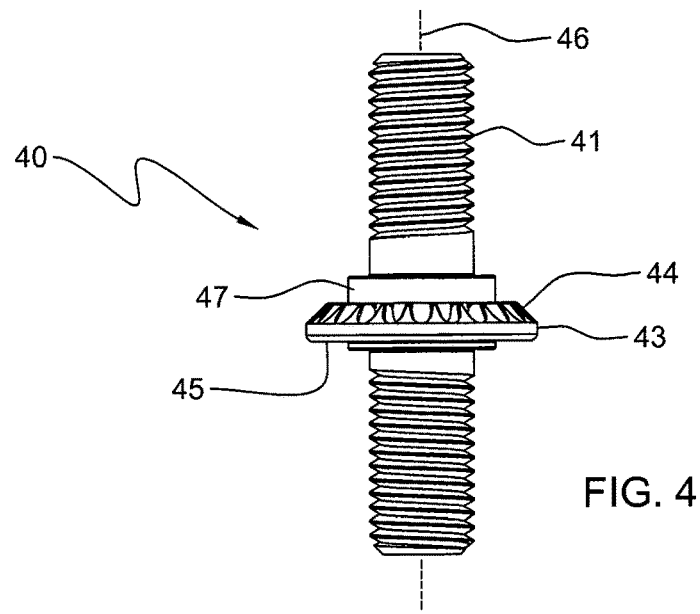
FIG. 4 is a side elevational view of a central rod member of the vertebral body replacement device of FIG. 1, in accordance with an aspect of the present invention.

FIGS. 1 and 4 show central rod member 40 having first or superior threaded portion 41 and a second or inferior threaded portion 42 with the two threaded portions having opposing thread configurations. This means that when first threaded portion 41 is constructed with right-handed threads, second threaded portion 42 is constructed with left-handed threads. It should be understood to those skilled in the art that the vice-versa thread configuration is also contemplated. Central rod member 40 further includes a central axis 46 that passes from first threaded portion 41 to second threaded portion 42 with a gear wheel portion 43 being positioned intermediate first threaded portion 41 and second threaded portion 42. Gear wheel portion 43 is generally constructed with a toothed face surface 44, the plane of toothed face surface 44 being oriented substantially perpendicular to central axis 46. Collar element 47 is positioned adjacent to tooth face surface 44 to ensure proper external access of tooth face surface 44 within middle chamber 36 following assembly of vertebral body replacement device 10. Further, gear wheel portion 43 includes support surface 45 that is located on the inferior aspect or underside of gear wheel portion 43. Similar to that described for toothed wheel surface 44, the plane of support surface 45 is correspondingly oriented substantially perpendicular to central axis 46. As explained previously, support surface 45 will contact and slidingly articulate with bearing surface 51 of support ring 50 (see FIG. 1) when vertebral body replacement device 10 is assembled and in use. Gear wheel portion 43 is integral to central rod member 40 and is positioned so that when gear wheel portion 43 is moved about its rotational axis, first threaded portion 41 and second threaded portion 42 will also rotate because gear wheel portion 43 axis of rotation is coaxial with central axis 46.

Figure 2A:
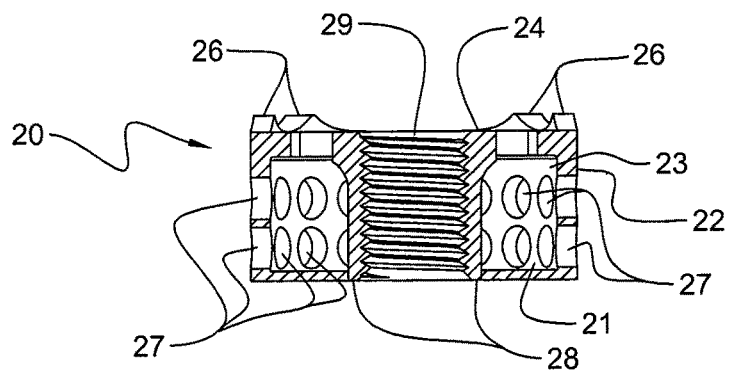
FIG. 2A is a cross-sectional, side elevational view of an end member of the vertebral body replacement device of FIG. 1 taken along line 2-2, showing an inner portion with a surrounding external wall, an internal wall and an end wall with the inner portion including a centrally oriented threaded housing element configured to engage a central rod member with the end wall being oriented normal relative to the external wall, in accordance with an aspect of the present invention.
Figure 2B:
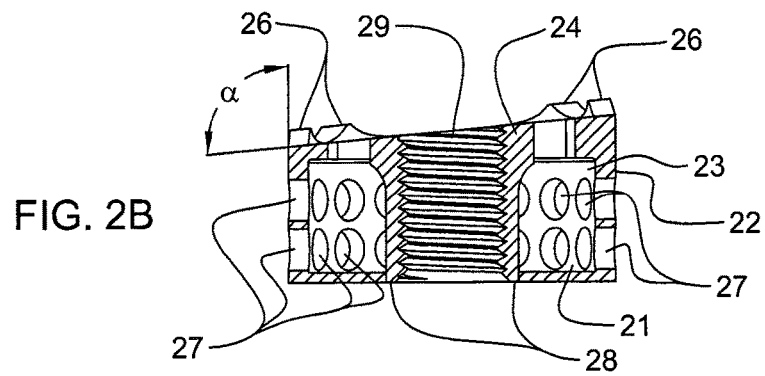
FIG. 2B is a cross-sectional, side elevational view of an alternative embodiment of an end member, showing an inner portion with a surrounding external wall, an internal wall and an end wall with the inner portion including a centrally oriented threaded housing element configured to engage a central rod member with the end wall being oriented at an angle relative to the external wall, in accordance with an aspect of the present invention.

FIGS. 1, 2A and 2B depict end member 20. Vertebral body replacement device 10 includes in its construct at least two end members 20, with the first one end member 20 being positioned superiorly relative to body member 30 and the second end member 20 being positioned inferiorly relative to body member 30. In operation, superiorly positioned first end member 20 is aligned and concentric with first end receptacle 33 so that when first end member 20 moves relative to body member 30, an internal wall 23 of end member 20 is continuously positioned adjacent to outer wall 32 of first end receptacle 33. The same operational relationship occurs with inferiorly positioned second end member 20 as it will be aligned and concentric with second end receptacle 34 so that when second end member 20 moves relative to body member 30, internal wall 23 of end member 20 is continuously positioned adjacent to outer wall 32 of second end receptacle 34.

As seen in FIGS. 2A and 2B, end member includes an inner portion 21 that is bounded by internal wall 23 and a centrally positioned threaded housing element 28. Threaded housing element 28 is constructed with internal threads 29 that may extend the full length of threaded housing element 28. Internal threads 29 are configured to correspondingly threadingly engage threaded portions 41, 42 of central rod member 40 upon assembly of vertebral body replacement device 10. Although not shown in FIGS. 2A and 2B, internal wall 23 also includes at least one channel 25 (see FIG. 1) with at least one channel 25 being oriented substantially vertical and is sized to receive corresponding at least one anti-rotational rib 35 of body member 30 when vertebral body replacement device 10 is assembled.

As further shown in the cross-sectional views of FIGS. 2A and 2B, end member 20 has an external wall 22, through which at least one hole 27 passes to adjacent internal wall 23. At least one hole 27 is sized to allow for the placement of bone graft material and other biocompatible materials for the purpose of facilitating a bone fusion bed following implantation.

Additionally, as seen in FIGS. 1 and 2A, end wall 24 functions to cap or bound inner portion 21 at one end of end member 20. End wall 24 is integrally coupled to threaded housing element 28 and generally includes at least one projection 26 or engagement element that extends in an outward direction from the outer surface of end wall 24. At least one projection 26 may be configured as a tooth-like body (as shown in FIGS. 1, 2A, 2B, and 5) although other shaped projections or engagement elements are contemplated including, but not limited to, spikes, pegs, grids, fingers and posts. At least one projection 26 is sized to allow for operative engagement with the adjacent vertebral body, more specifically with the anatomic end plate of the vertebral body to provide adequate fixation post-implantation and to withstand any torsional loads that may be applied to end member 20 following implantation and during the lengthening procedure of vertebral body replacement device 10.

Cross-section view of FIG. 2A shows, end wall 24 being oriented perpendicular or normal relative to external wall 22. FIG. 2B shows an alternative embodiment of end member 20 with end wall 24 being oriented at an angle α and relative to external wall 22. Having end wall 24 being angled provides the operating surgeon with the ability to treat clinically, lordotic and kyphotic deformities. It should be well understood to those skilled in the art that end member 20 will be offered in a wide range of degrees of angulations in varying increments from 0° to 20°, thereby providing the operating surgeon with the ability to precisely treat any deformity presented during a surgical procedure.

Figure 11A:
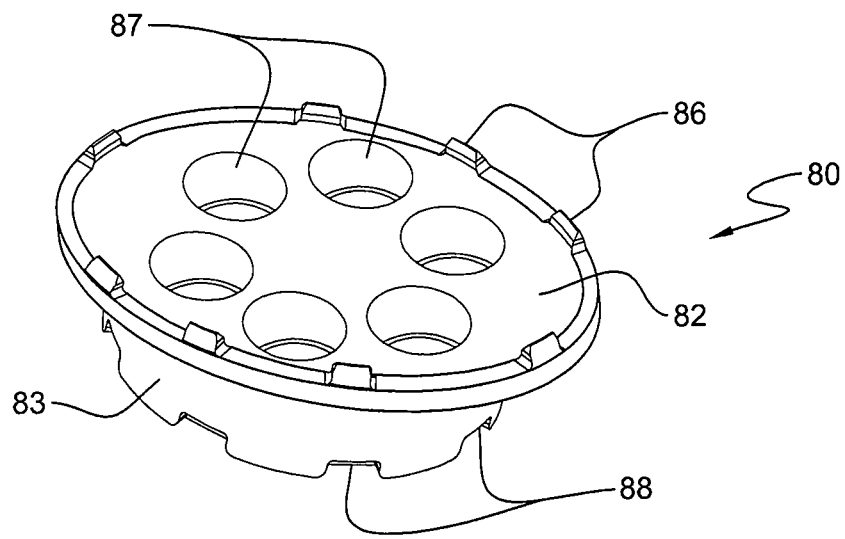
FIG. 11A is a perspective view of another alternative embodiment of a detachable footplate member.
Figure 11B:
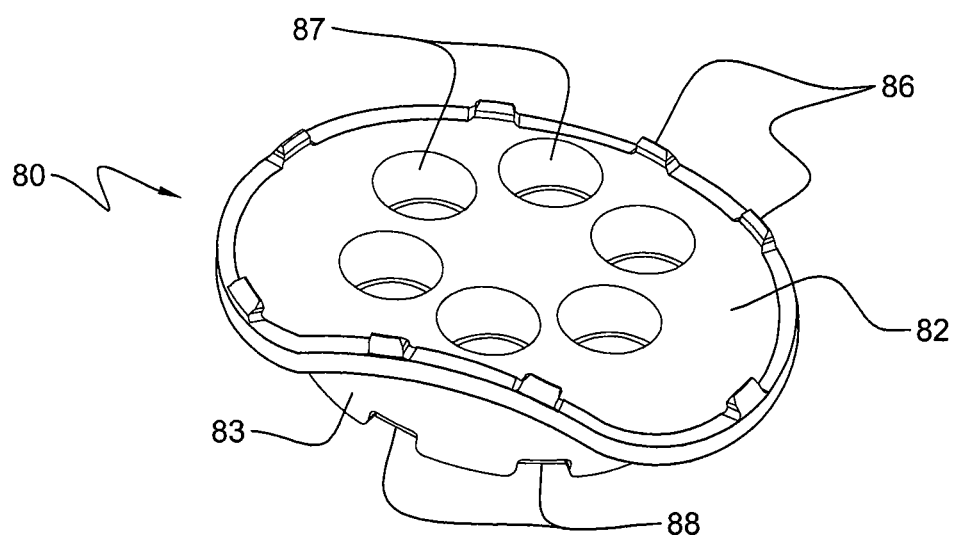
FIG. 11B is a perspective view of another alternative embodiment of a detachable footplate member.

As shown in FIG. 9, it is contemplated that, vertebral body replacement device 10 may include an alternative embodiment of end member 90, with end wall 94 being configured to couple a footplate member 80. End wall 94 may further include at least one alignment tab 91 that functions to orient footplate member 80 in the preferred position relative to end member 90 and a vertebral body following implantation. As seen in FIGS. 11A and 11B, it is contemplated that footplate member 80 will be available in a plurality of various circular, non-circular and polygonal outer profile shapes, (i.e., circular as shown in FIG. 9, oval as shown in FIG. 11A, kidney as shown in FIG. 11B or oblong (not shown)) and sizes. It is further contemplated that footplate member 80 will be available in varying thicknesses or heights T as seen in FIG. 10A. Having a kit or implant system that includes a range of various sized heights, shapes, sizes and angled footplate members 80 provides the operating surgeon with multiple choices to maximum bone coverage, spine alignment and resulting stability of the device relative to the adjacent vertebral body following implantation.

As shown in FIG. 10A, an end surface 82 may be configured in a neutral or normal orientation relative to a sidewall 83 of footplate member 80. Alternatively, FIG. 10B shows footplate member 80 having end surface 82 being angled (angle Δ) relative to sidewall 83. As discussed above, it is contemplated that the operating surgeon will be provided with a plurality of footplate members 80 each having a different angle, with angulation ranging from 0° to 20°. Having such a wide range of incrementally angled footplate members 80 available will provide the operating surgeon with the ability to customize the vertebral body replacement device 10 during the operative procedure to meet the presented clinical deformity. Although shown with a circular perimeter geometry in FIG. 9, as described previously it should be understood to those skilled in the art that both neutral and angled footplate members 80 will be constructed in multiple outer profile geometric shapes, sizes and overall thickness T, again to provide the operating surgeon with the ability to maximize bone support post-implantation. Footplate member 80 may be modular in design, thereby allowing the operating surgeon to mix and match and interchange footplate members 80 with end member 90. This is accomplished by securely attaching and allowing detachment of footplate member 80 from end wall 94 of end member 90 by use of a locking mechanism 84. For example purposes only, as shown, locking mechanism 84 may consist of at least one locking screw 85 that passes through a hole 87 in end surface 82 to engage corresponding threaded holes 92 in end wall 94. Further, it should be understood to those skilled in the art that various other low-profile locking or securement mechanisms may also be used for this purpose including, but not limited to lock pins, bolts, and press fit pins. As described above, it is contemplated that footplate member 80 will also include at least one projection 86 or engagement element that extends outwardly from the end surface 82. At least one projection 86 may be configured as a tooth-like projection (as shown in FIGS. 9, 10A, and 10B,) although other shaped engagement elements are contemplated, including but not limited to, spikes, pegs, grids, figures and posts. End surface 82 may be treated or coated with certain materials to facilitate bio-ingrowth with the adjacent vertebral body following implantation. Additionally, end surface 82 may also undergo a process or treatment that results in end surface 82 having nano-sized or micron-sized surface features. In addition, footplate member 80 may have an orientation mechanism 93 that may include alignment slots 88 that slidingly engage corresponding tabs 91 positioned around the peripheral of end member 90. Orientation mechanism 93 functions to securely orient footplate member 80 relative to end wall 94 and the adjacent vertebral body.

As seen in FIG. 9, footplate member 80 has an orientation or adjustment mechanism 93 that may include alignment slots 88 that are positioned along mating surface or sidewall 83. Slots 88 will slidingly engage corresponding tabs 91 positioned around the peripheral of end member 90. Orientation or adjustment mechanism 93 functions to facilitate the positioning of footplate member 80 relative to end member 90 and more specifically to end wall 94 and ultimately when implanting, the adjacent vertebral body within the spinal column of a patient. Footplate member 80 when moved is typically rotated or moved relative to central axis 89 and end member 90. It is contemplated further that an alternative embodiment of orientation or adjustment mechanism 93 may be positioned in the more central portions of end wall 94 and end surface 82, respectively.

Figure 5:
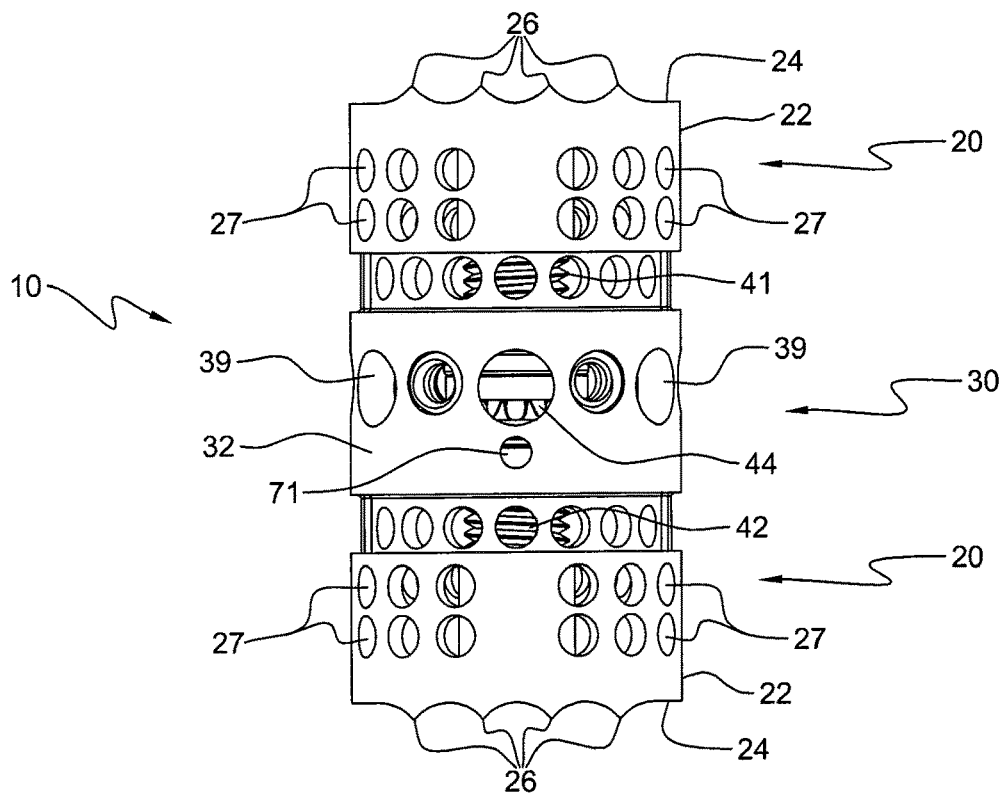
FIG. 5 is a side elevational view of the assembled vertebral body replacement device of FIG. 1, showing a superiorly positioned end member and an inferiorly positioned end member extended away from the body member, in accordance with an aspect of the present invention.
Figure 6:
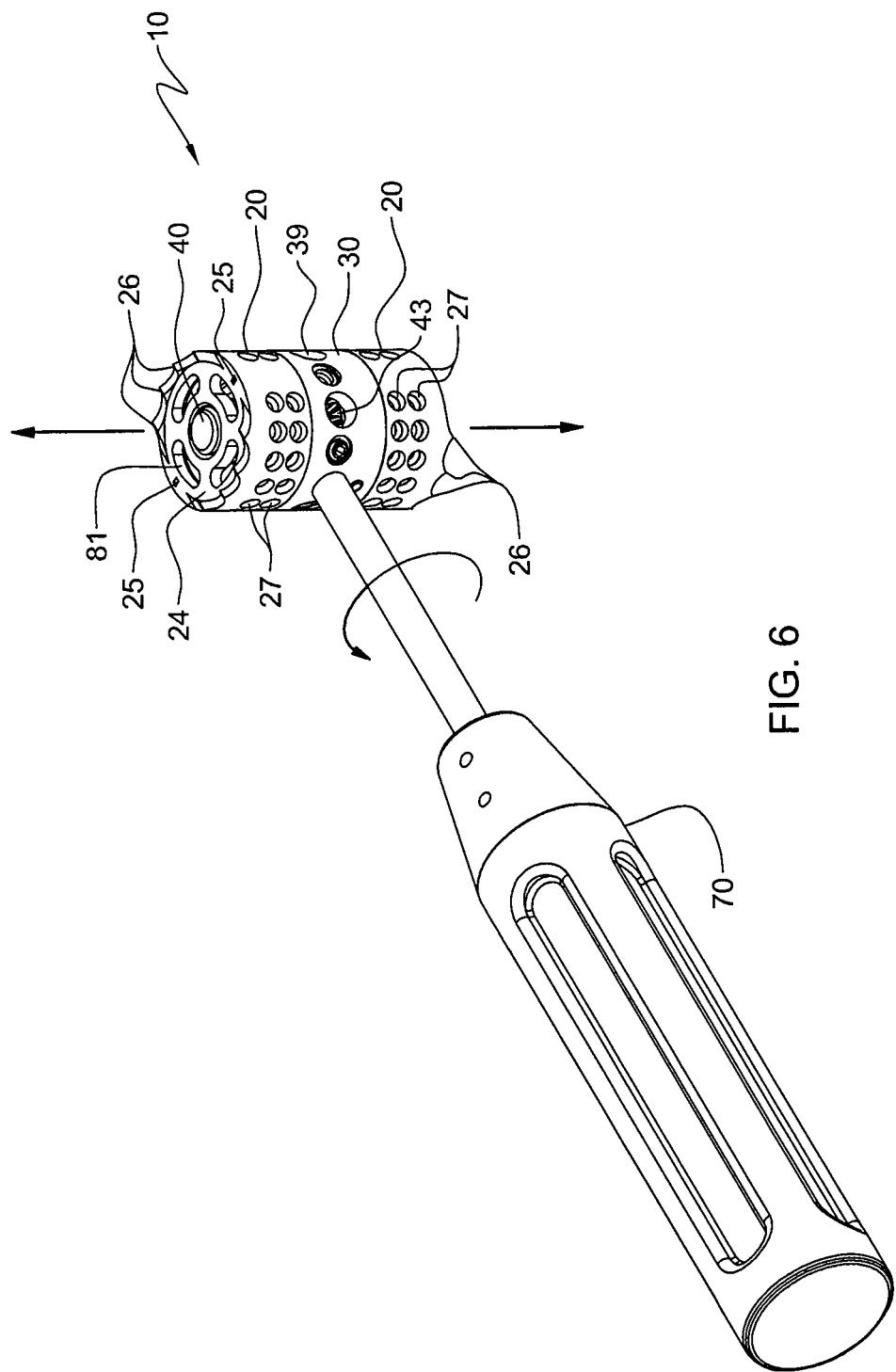
FIG. 6 is a perspective view of the vertebral body replacement device of FIG. 1, with a tool inserted through a tool port hole and in operable position with the central rod member, in accordance with an aspect of the present invention.

Following the assembly of vertebral body replacement device 10, superiorly positioned or first end member 20 and inferiorly positioned or second end member 20 are both positioned with each respective inner portion 21 and threaded housing element 28 within first end receptacle 33 and second end receptacle 34, respectively. As shown in FIG. 6, first end member 20 and second end member 20 may be simultaneously extended or retracted in an axial direction relative to body member 30 resulting in either the lengthening or shortening of the over-all length of vertebral body replacement device 10 by inserting a tool 70 through tool port hole 39 to engage the gear shaped tip (not shown) of tool 70 with tooth faced surface 44 of gear wheel portion 43 of central rod member 40. In operation, tool 70 is rotated causing gear wheel portion 43 to rotate resulting in first and second threaded portions 41, 42 rotating about central axis 46. When assembled, threaded housing element 28 of first and second end members 20 are threaded onto first and second threaded portions 41, 42 of central rod member 40 respectively, with at least one channel 25 of first and second end members 20 also engaging at least one anti-rotational rib 35 positioned on outer wall 32 of first and second end receptacles 33, 34, respectively. Functionally, the engagement of at least one channel 25 of first and second end members 20 with at least one rib 35 of body member 30 prohibits rotational movement of the first and second end members 20 when tool 70 is turned, thus resulting in first and second end members 20 simultaneously advancing or moving in opposing axial directions relative to body member 30 for a maximum distance equal to the thread length of first and second thread portions 41, 42 of central rod member 40. As discussed above, the bi-directional axial motion of the first end and second end members 20 is caused by the opposing threads (i.e., right-handed and left handed threads) of the respective first and second threaded portion 41, 42 of the central rod member 40. Operationally, central rod member 40 converts the rotational motion of tool 70 and gear wheel portion 43 into corresponding axial or linear movement of first and second end members 20, with the mating of channel 25 and rib 35 substantially prohibiting any rotational movement of two end members 20 relative to longitudinal axis 72 and the adjacent vertebrae, thus eliminating torsional forces being applied to the end member-vertebral body interface. For example purposes, FIG. 5 shows an assembled vertebral body replacement device 10 following partial simultaneous movement of first and second end members 20 as describe above.

Figure 8:
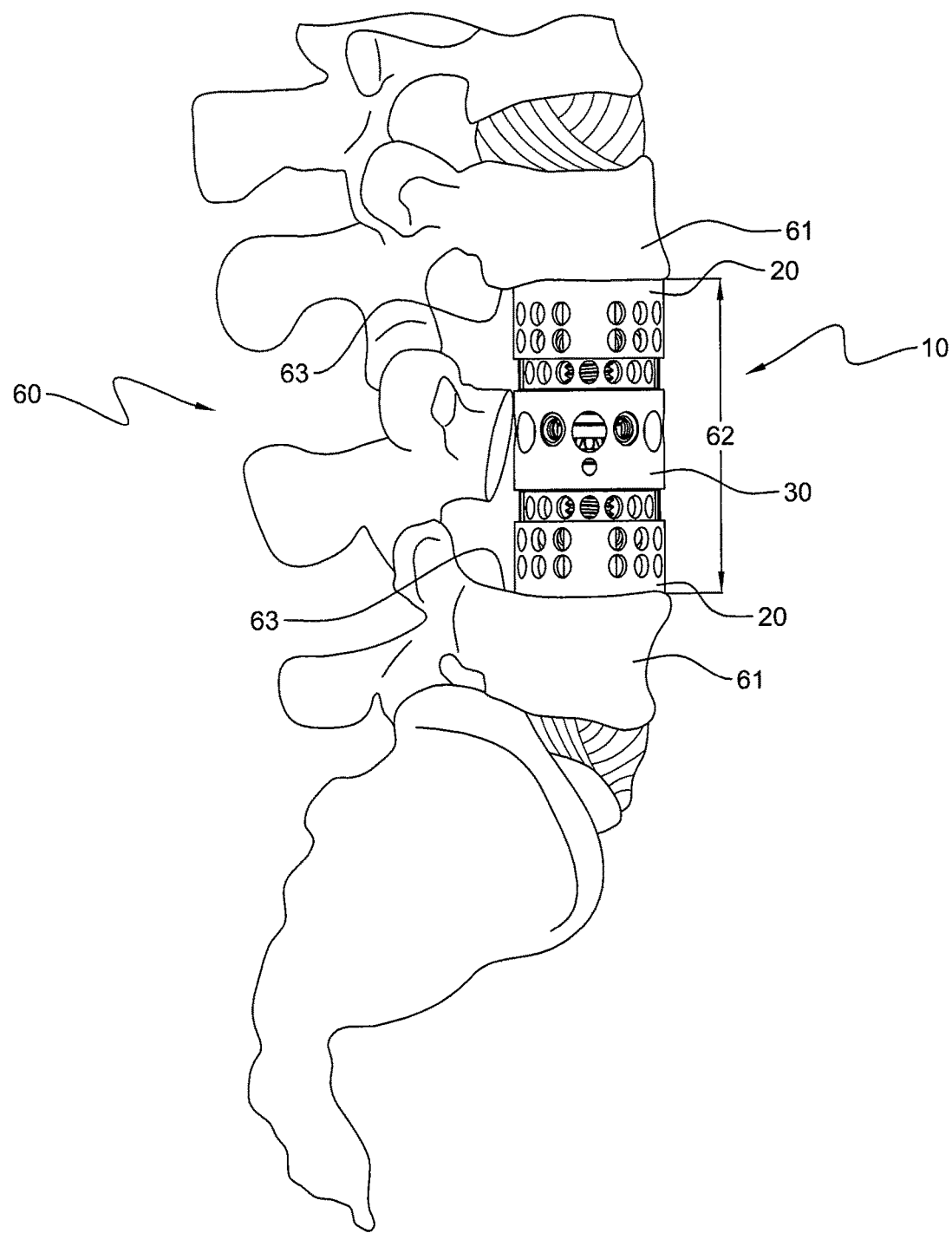
FIG. 8 is a side elevational view of the vertebral body replacement device of FIG. 1, shown positioned between two vertebral bodies with the superiorly positioned end member and the inferiorly positioned end member extended to maintain a desired space within a spinal column, in accordance with an aspect of the present invention.

FIG. 8 shows assembled vertebral body replacement device 10 positioned within a space between two vertebral bodies following simultaneous movement of first and second end members 20 in the manner described above, resulting in intimate contact between an adjacent vertebral body and at least one projection 26 extending from end wall 24, or alternatively, projection 86 of footplate member 80 (not shown). A resultant compressive force is applied by each end member 20 (or footplate member 80) against the contacted vertebral body to maintain the desired anatomic spacing.

The surgical technique for implantation of a vertebral body replacement device is well known in the art, including the appropriate surgical exposure and dissection techniques. The method includes, obtaining a vertebral body replacement device 10 that may include body member 30, central rod member 40 that has two threaded portions 41, 42 and is configured to be operatively associated within body member 30 and first and second end members 20 that are configured to threadingly engage the two threaded portions 41, 42 of central rod member 40. As discussed above, body member 30 and end members 20 are further configured to inhibit rotational movement of two end members 20 following assembly and positioning of vertebral body replacement device 10 within a space within a spinal column with both end members 20 engaging respective vertebral bodies when central rod member 40 is rotationally actuated, thus causing two end members 20 to move in opposing axial directions relative to body member 30. Upon such movement, two end members 20 will apply a force to the two adjacent vertebral bodies within the spinal column. It should be understood that all of the above noted device components and respective elements include the same structural and functionality characteristics as described previously herein.

Figure 7:
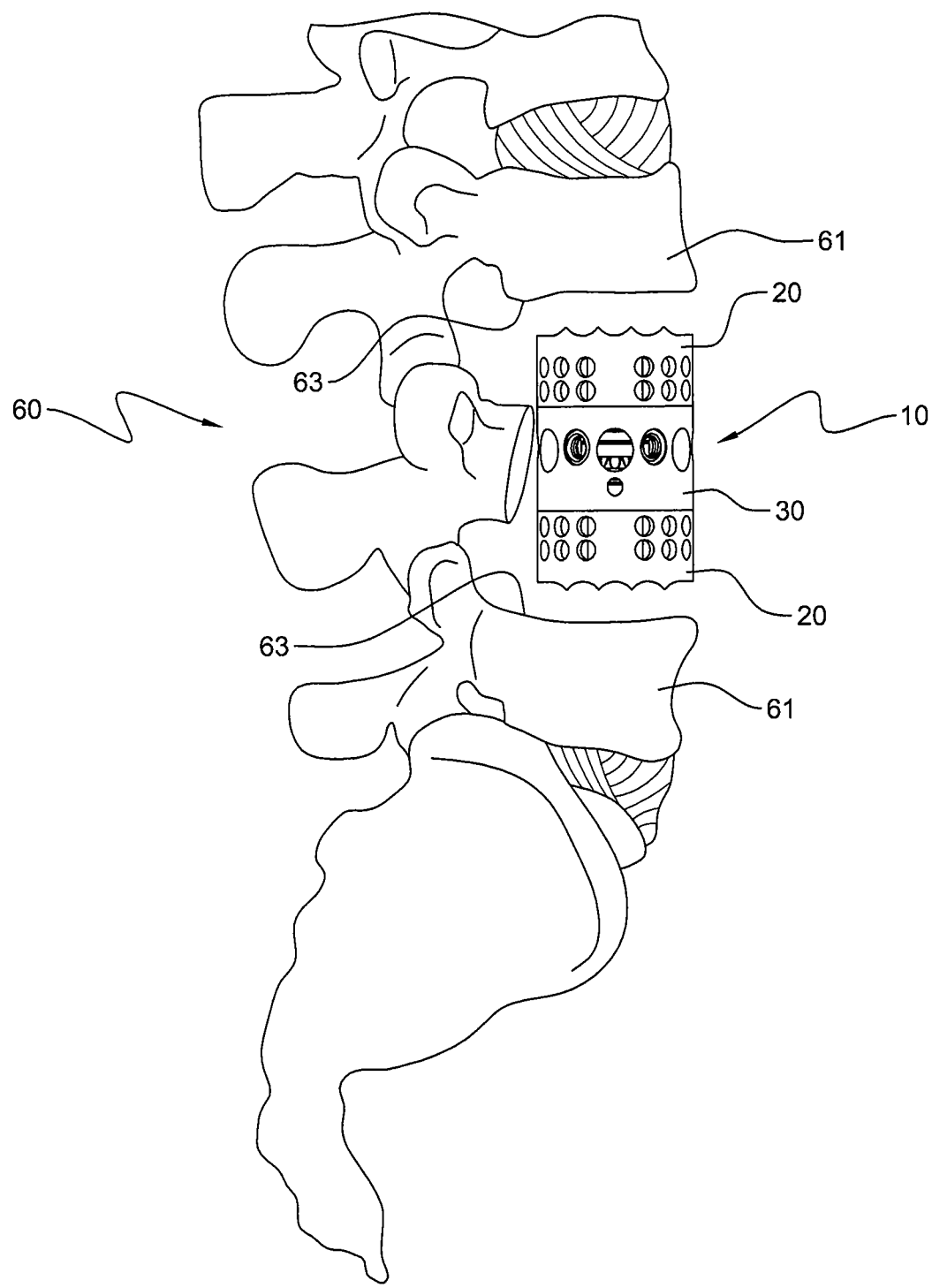
FIG. 7 is a side elevational view of the vertebral body replacement device of FIG. 1, shown disposed within a space between two vertebral bodies within a spinal column prior to the translational movement of the superiorly positioned end member and the inferiorly positioned end member, in accordance with an aspect of the present invention.

As seen in FIG. 7, the method may further include the step of positioning vertebral body replacement device 10 between two vertebral bodies within a patient's spinal column. The surgical method may also include the step of simultaneously operatively moving in opposing directions both end members 20 relative to body member 30 to produce a force against the two respective adjacent vertebral bodies for the purpose of maintaining a space between the two vertebral bodies within the spinal column as shown in FIG. 8. Although not shown, the method may further include the step of engaging tool 70 with central rod member 40 through tool portal hole 39, whereby rotary motion of tool 70 is converted into opposing axial movement of two respective end members 20 relative to body member 30 causing two end members 20 to come in contact and apply a force to the adjacent vertebral bodies, thereby maintaining the space between these two vertebral bodies. The method also may include the step of securely coupling to body member 30 a lock pin through lock pin hole 71 following finalization of the length adjustment procedure to ensure securement of two end members 20 relative to body member 30 and central rod member 40.

It should be understood by those skilled in the art that the surgical method described herein may also include alternatively, using the modular footplate member 80 that has been coupled to alternative embodiment end member 90 which has been more fully described above. The sequence of implantation of vertebral body replacement device 10 as described herein may be different depending upon the given clinical situation and whether footplate members 80 are attached on the "back table" prior to the complete assembly of vertebral body replacement device 10 or within the operative site. The sequence of device assembly will be at the discretion of the operating surgeon and will vary depending upon the preference of the operating surgeon in combination with the clinical needs of the patient.

It is further contemplated that an implant system comprised of various cross-sectional sizes, cross-sectional polygonal and circular/oval shapes and longitudinal lengths of body members 30, end members and footplate member 80 will be available as a kit. This will allow the operating surgeon to pick and choose the separate member components to assemble vertebral body replacement device 10 that best fits into a certain spinal segment or to address an anatomical deformity presented in a patient. It should be understood by those skilled in the art that each shaped and dimensioned member provided will function in the same manner as described previously herein with central rod member 40 and supporting ring 50.

Also disclosed herein is a surgical instrument for use in inserting an implant into a space between two bones. More specifically, the surgical instrument will typically be used to hold, extend/contract and lock a vertebral body replacement implant during implantation into the spinal column. The surgical instrument generally includes a handle assembly, an elongate member that includes an implant engagement assembly at the distal end. The implant engagement assembly further includes an actuation body and an implant holding portion that has two arms that move and grasp the implant when the actuation body is actuated. The surgical instrument further includes a length control mechanism and locking mechanism. The distal end or gear assembly of the length control mechanism is inserted into the implant and couples to a corresponding length adjustment mechanism to allow for varying the overall length of the implant. The surgical instrument typically further includes a locking mechanism that provides for the insertion of a locking pin or screw into the implant to fix the overall length of the implant.

As used herein, the terms "surgical instrument" and "inserter" may be used interchangeably as they essentially describe the same type of operative instrument. Further, described herein is a surgical method for using the surgical instrument, a method of fabricating the surgical instrument and a spinal implant insertion kit that is used to maintain a space between two vertebrae within a patient suffering from a diseased or damaged spinal column.

Figure 12:
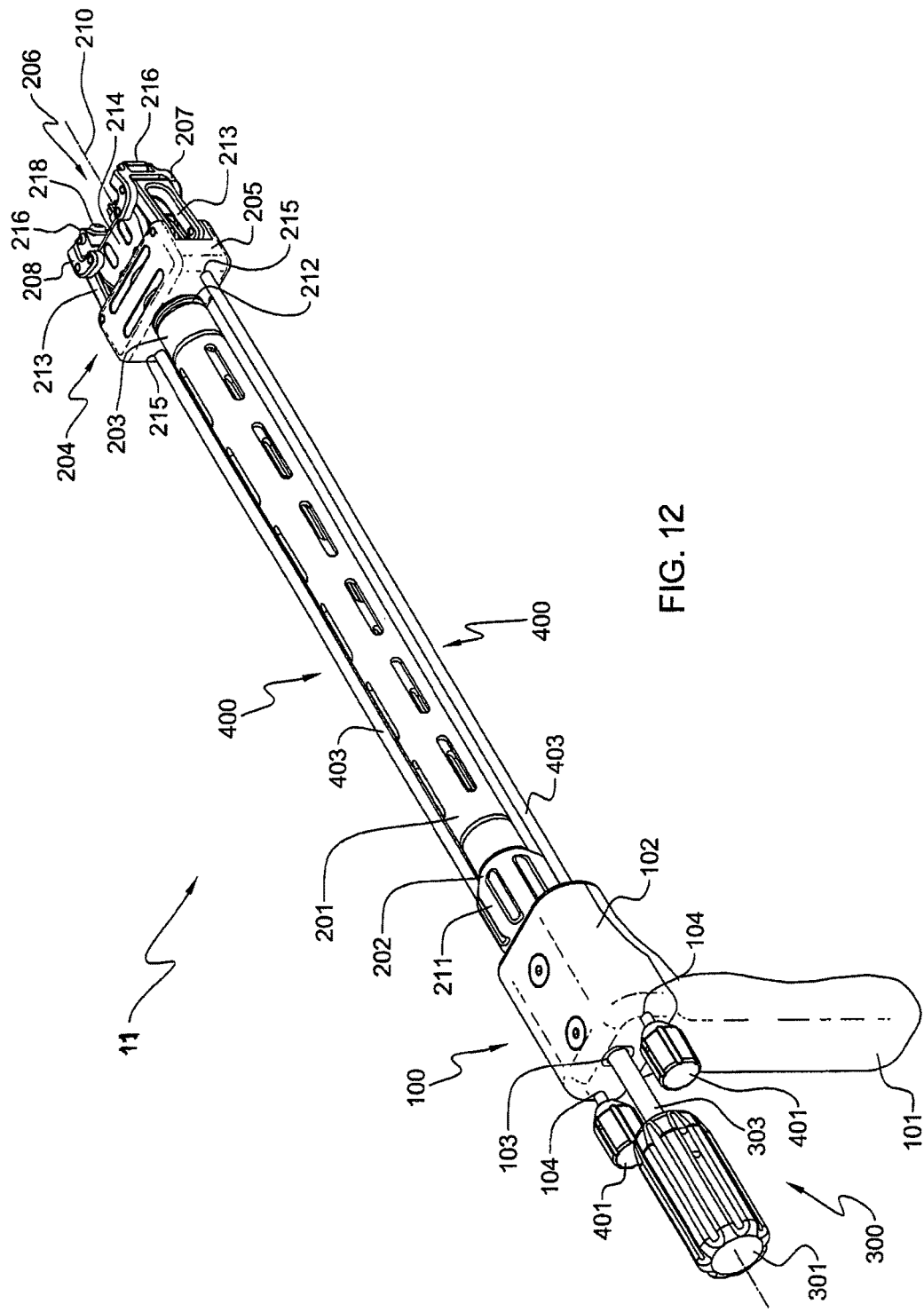
FIG. 12 is a perspective view of one embodiment of a surgical instrument, in accordance with an aspect of the present invention.
Figure 14:
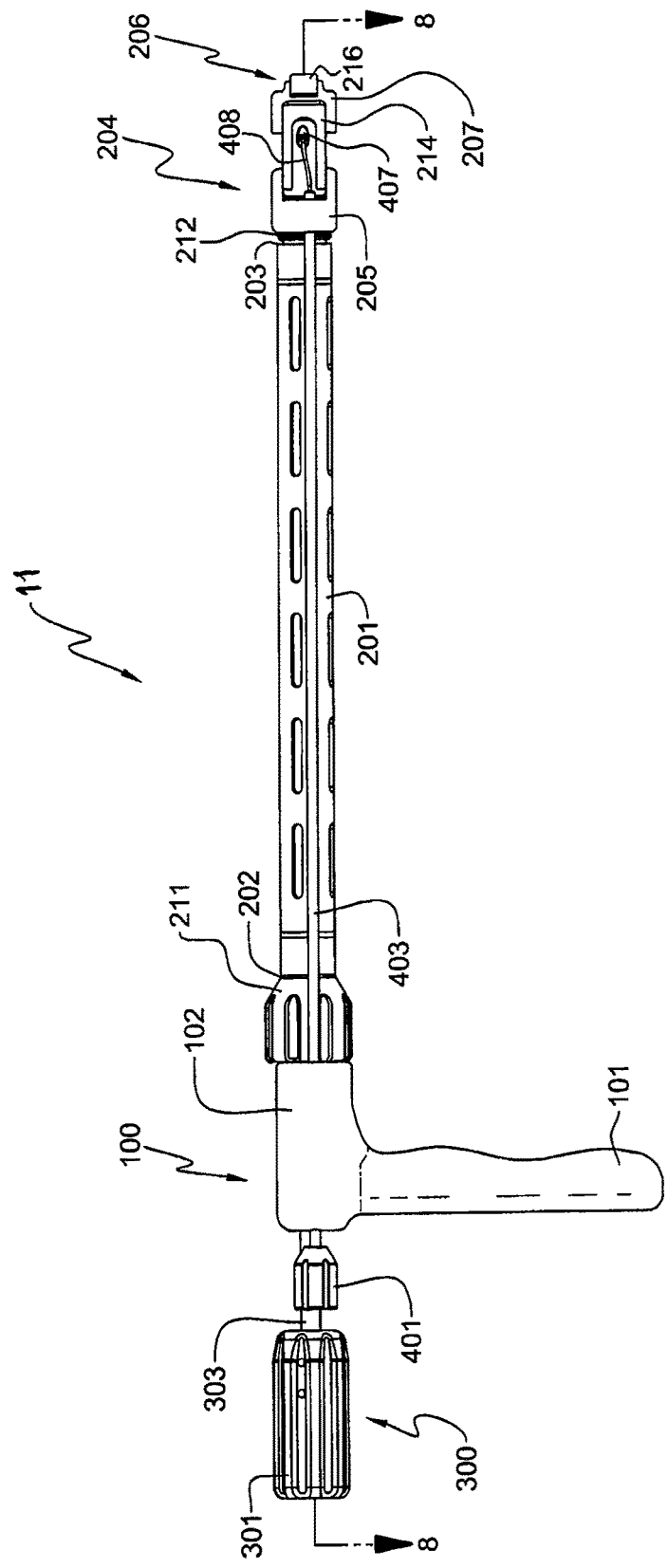
FIG. 14 is a side elevational view of the surgical instrument of FIG. 12, in accordance with an aspect of the present invention.
Figure 15:
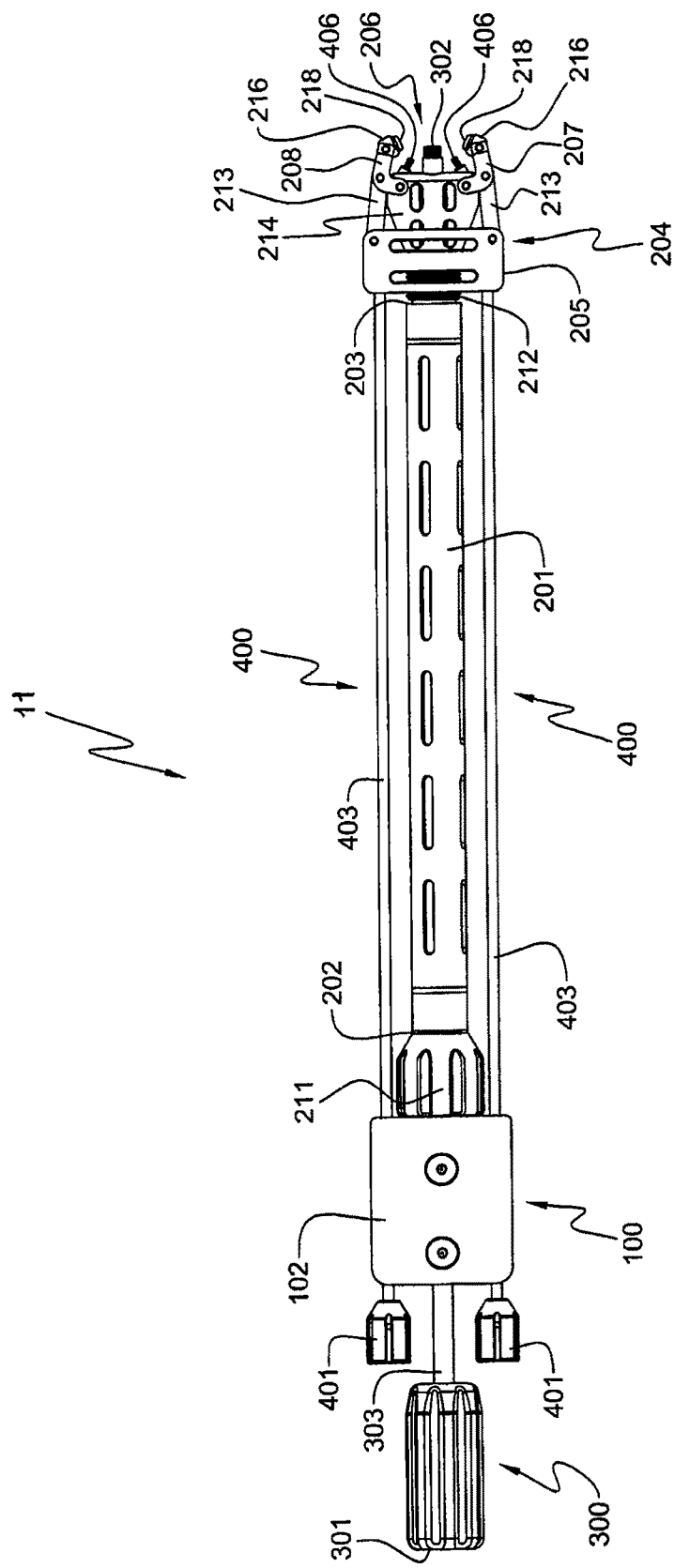
FIG. 15 is a top view of the surgical instrument of FIG. 12, in accordance with an aspect of the present invention.

As depicted in FIGS. 12, 14 and 15, the general arrangement of a surgical instrument 11, in accordance with an aspect of the present invention, includes a handle assembly 100, an elongate member 201, an implant engagement assembly 204, a length control mechanism 300, and at least one locking mechanism 400. Surgical instrument 11 is to be used to grasp, expand and contract the length and secure the overall length of the implant when placed within the body. One type of implant that may be used with surgical instrument 11 is the one described in U.S. patent application Ser. Nos. 11/928,532 and 11/928,553. The contents and disclosure provided in these U.S. applications are hereby incorporated herein by reference.

In this detailed description and the following claims, the words proximal, distal, anterior, posterior, medial, lateral, superior and inferior are defined by their standard usage for indicating a particular part of a bone, prosthesis or surgical instrument according to the relative disposition of the surgical instrument or directional terms of reference. For example, "proximal" means the portion of an instrument positioned nearest the torso, while "distal" indicates the part of the instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

With reference to FIGS. 12 and 14, surgical instrument 11 includes handle assembly 100, elongate member 201, implant engagement assembly 204 that further includes an actuation body 205, an alignment body 214 and a holding portion 206. Further included in surgical instrument 11 is length control mechanism 300 and at least one locking mechanism 400 that is oriented to run parallel to a longitudinal axis 210 of elongate member 201.

As shown in FIG. 12, handle assembly 100 of surgical instrument 11 also includes a body portion 101 and a top portion 102. Body portion 101 is generally configured as a grip or holder to accommodate the palm and fingers of the operating surgeon. It is contemplated that body portion 101 may be available in varying sizes and configurations to allow for surgical instrument 11 to be used in a wide range of surgical applications, including endoscopic procedures and approaches as well as fit various user hand sizes without sacrificing dexterity and comfort. Centered in top portion and extending in proximal to distal direction is at least one through hole 103. Hole 103 is sized to receive and fix a distal projecting cannulated tube 304 (see FIG. 19) that houses a drive shaft 303 that is a component of length control mechanism 300.

Figure 19:
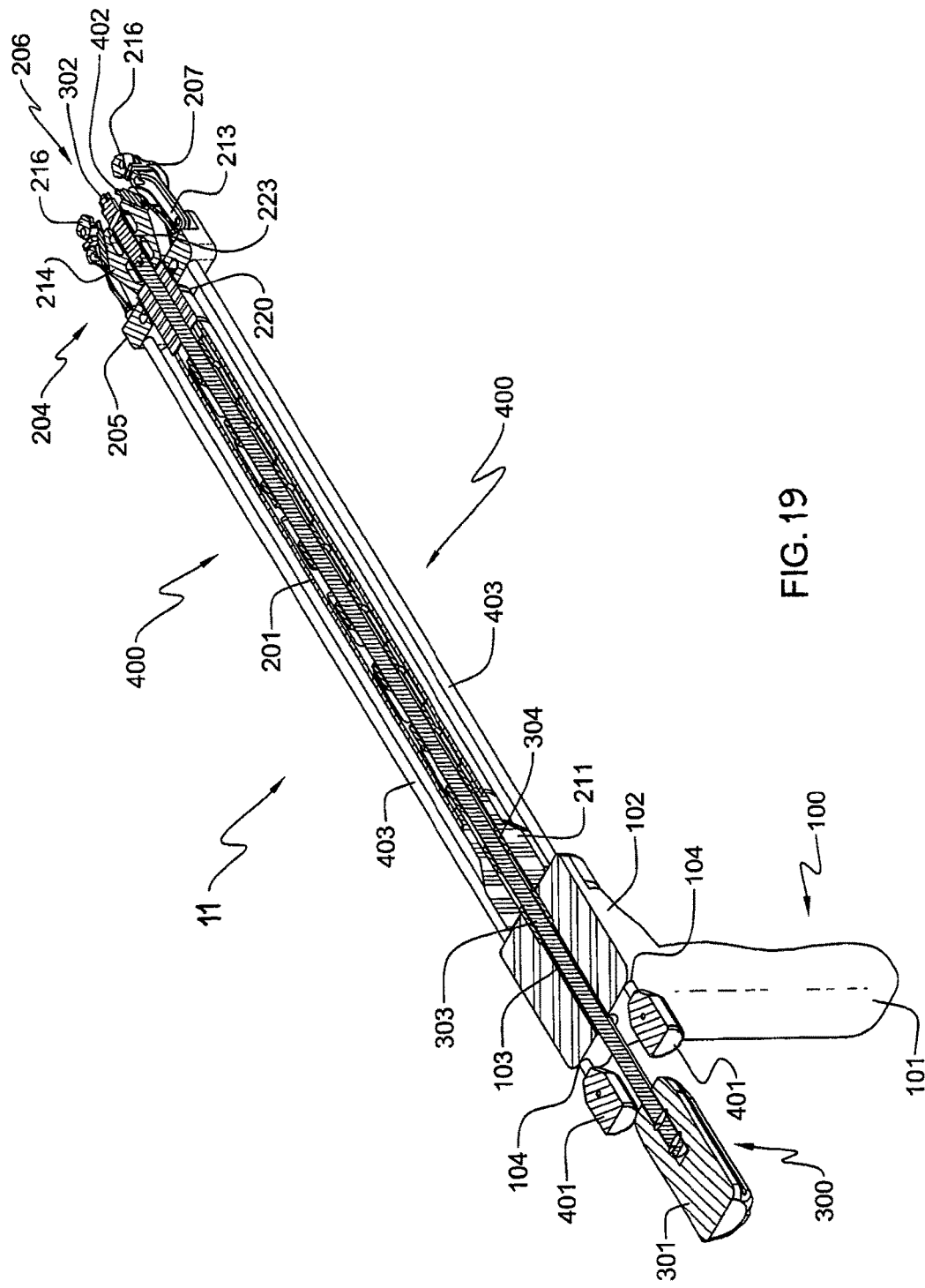
FIG. 19 a cross-sectional, perspective view of the surgical instrument of FIG. 12 taken along line 19-19, showing a top portion of the handle assembly, the elongate member and the implant engagement assembly, the length control mechanism and the locking mechanism, in accordance with an aspect of the present invention.

As seen in FIGS. 12 and 19, positioned on either side of hole 103 are two substantially parallel through holes 104 that are sized to receive the connecting rods 403 for the at last one locking mechanism 400. The embodiment shown for example purposes in FIG. 19, depicts two substantially parallel holes 104 that are sized to receive connecting rod 403 of locking mechanism 400. Holes 104 are configured to allow rotary motion of connecting rod 403 when an operating surgeon is using surgical instrument 11 to secure the overall length of an implant.

Positioned intermediate handle assembly 100 and actuation body 205 is elongate member 201. FIGS. 12, 14 and 15 show elongate body 201 extending in a proximal to distal direction with a first end 202 being located adjacent to handle assembly 100 and a second end 203 being moveably or rotatably connected to distally positioned implant engagement assembly 204 or more specifically, to actuation body 205. As seen in FIGS. 12-15, elongate member 201 is tube-like in structure with a round cross-sectional shape, although it is further contemplated that various geometric shaped cross-sections may be used in constructing elongate member 201, including, but not limited to oval, square, square, rectangular and other polygonal shapes. Further, as shown in FIG. 19, elongate member 201 is hollow with the inner diameter being sized to accommodate and surround cannulated tube 304. First end 202 is generally shaped as a gripping portion 211 with the configuration providing the operating surgeon with increased surface area and texture to grip and turn elongate member 201 when necessary. Second end 203 is typically configured to include a set of external threads 212 that will threadingly engage actuation body 205. When the operating surgeon rotates elongate member 201, the engaged actuation body 205 moves distally resulting in holding portion 206 engaging and grasping the implant. If the operating surgeon were to reverse the direction of rotation of elongate member 201, this would result in engaged actuation body 205 moving proximally relative to elongate member 201 and cause holding portion 206 to expand and release the implant from between first and second arms 207, 208.

Figure 13:
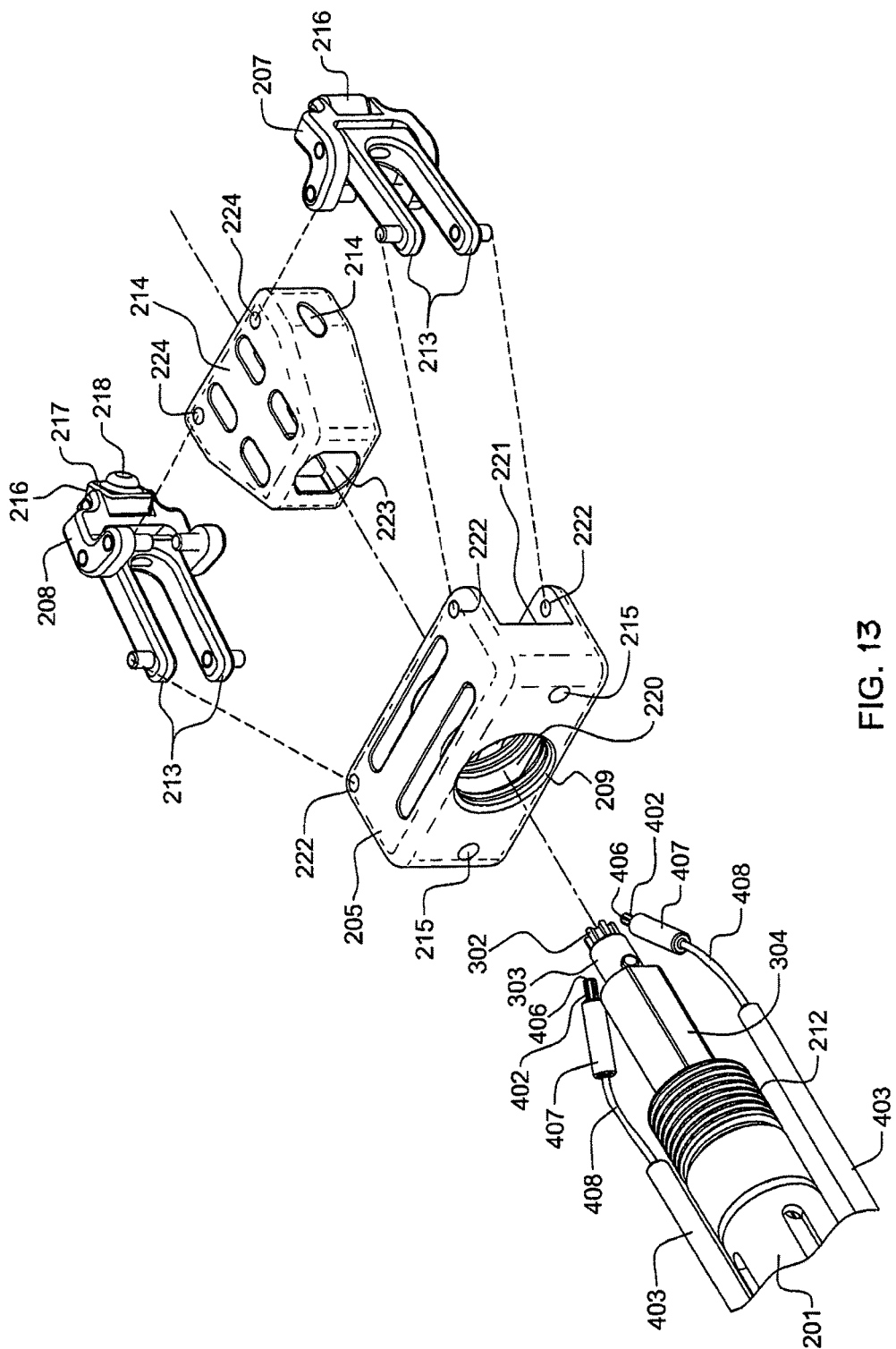
FIG. 13 is an enlarged, exploded perspective view of a distal end of the surgical instrument of FIG. 12 showing the distal aspects of an elongate member and a locking mechanism with an implant engagement assembly that includes an actuation body, a holding portion and an alignment body, in accordance with an aspect of the present invention.

FIG. 13 is an exploded view that shows implant engaging assembly 204 in more detail, specifically actuation body 205 and holding portion 206. Actuation body 205 may further be constructed to include a through central hole 220 with internal threads 209 that engage external threads 212. At least two through holes 215 are laterally positioned and may be sized to receive connecting rods 403. A slotted transverse opening 221 that is sized to slidingly engage the alignment body 214 is positioned in the distal aspect of actuation body 205. Connecting holes 222 for coupling the drive links 213 may also be constructed in the superior and inferior surfaces of the distal aspect of actuation body 205. A through hole 223 is positioned along the midline of alignment body 214 and it is sized to receive cannulated tube 304 and drive shaft 303. In addition, alignment body 214 may include fixation holes 224 that allow for the moveably coupling of arms 207, 208.

Figure 16:
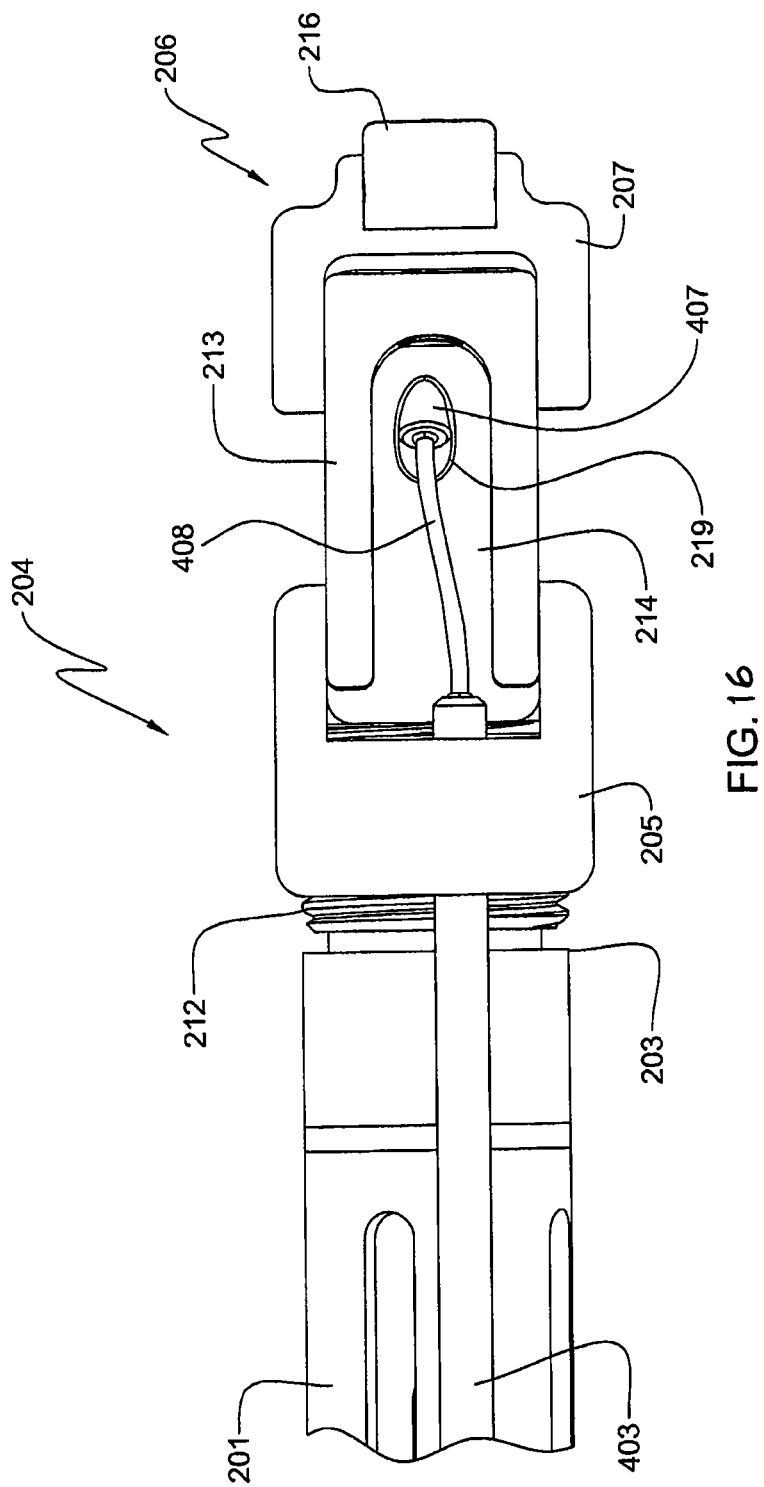
FIG. 16 is an enlarged, side elevational view of the assembled distal end of the surgical instrument of FIG. 12 showing the elongate member with external threads, the locking mechanism with a bearing portion, the implant engagement assembly, including the actuation body and holding portion with engagement member and the alignment body, in accordance with an aspect of the present invention.
Figure 17:
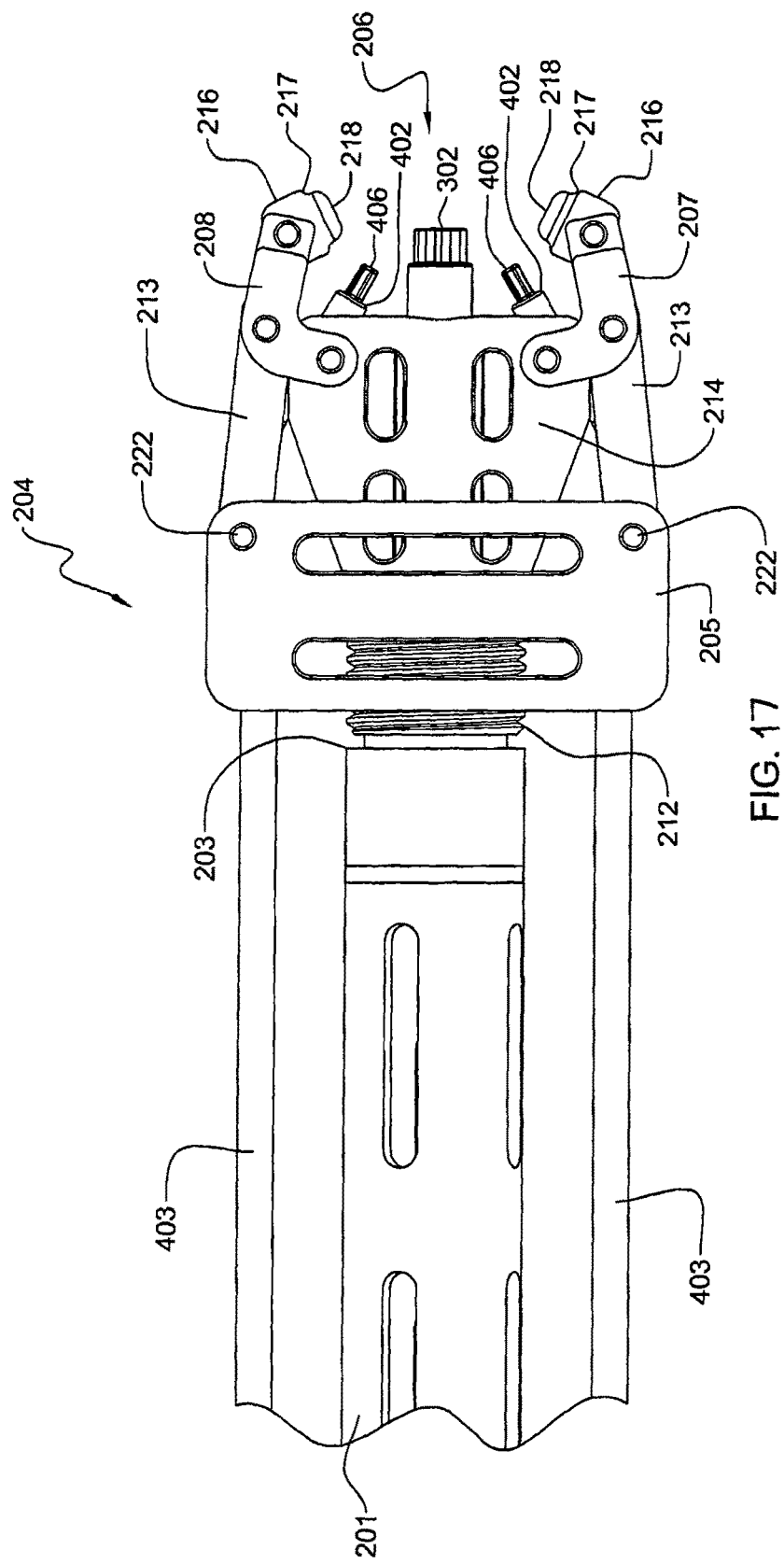
FIG. 17 is an enlarged, top view of the assembled distal end of the surgical instrument of FIG. 12 showing the elongate member with external threads, the locking mechanism with a coupling end, the implant engagement assembly, including the actuation body and the holding portion that includes the first and second arms and corresponding engagement members and the alignment body. Also seen, is the distal end of a length control mechanism, including a gear assembly, in accordance with an aspect of the present invention.
Figure 18:
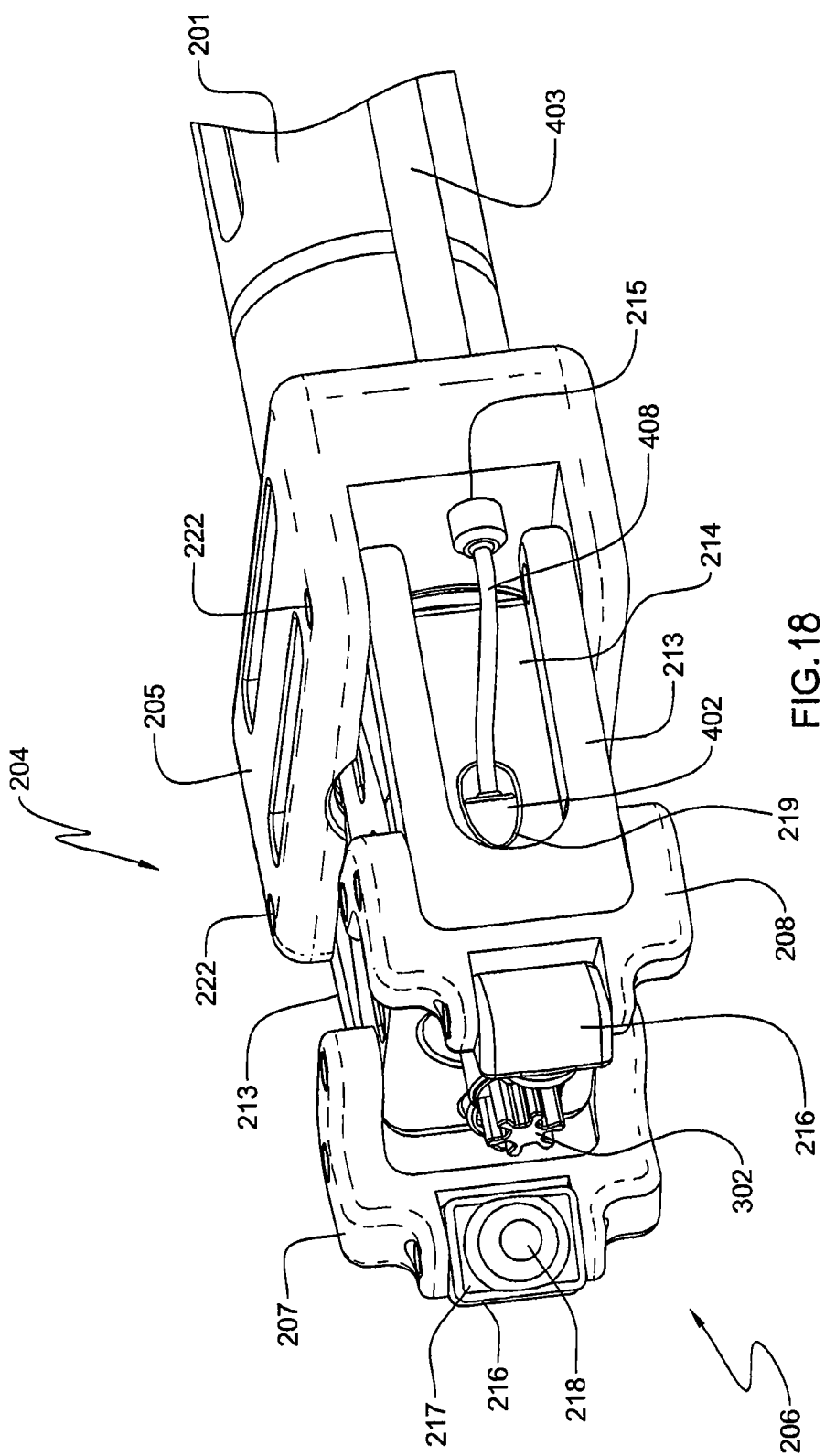
FIG. 18 is an enlarged, perspective view of the assembled distal end of the surgical instrument of FIG. 12 showing the elongate member, the locking mechanism with the bearing portion, the implant engagement assembly including the actuation body and the holding portion that includes the first and second arms with the corresponding engagement members and the alignment body. Also seen, is the distal end of the length control mechanism with the gear assembly, in accordance with an aspect of the present invention.

Holding portion 206 as seen in FIGS. 16-18 generally includes alignment body 214, drive links 213, first arm 207 and second arm 208 with attached engagement members 216 positioned at the distal aspect of the first and second arms 207, 207. Holding portion 206 is constructed to allow for first and second arms 207, 208 to move in a direction towards the midline of surgical instrument 11 and then away from the midline when drive links 213 are moved either distally or proximally, respectively.

As seen in FIG. 17, drive links 213 are attached to actuation body 205, therefore as discussed above, when elongate member 201 is threaded into actuation body 205 and move actuation body 205 in either a distal or proximal direction, the distally attached drive links 213 will then cause first and second arms 207, 208 to move either towards the midline or away from the midline. First and second arms 207, 208 are generally configured as L-shaped bodies to facilitate continuous movement when coupled to drive links 213.

FIGS. 13 and 17 also depict the two engagement members 216 that are positioned at the distal ends of first and second arms 207, 208. Engagement members 216 are attached to the distal ends of first and second arms 207, 208 in a manner that allows engagement members 216 to pivot and rotate around the arm ends. This pivoting motion coupled with the movability of arms 207, 208 allows surgical instrument 11 to accommodate a broad range of sizes of implants including implants with variable widths or diameters. Engagement members 216 have a distal surface 217 that includes an attached engagement element 218 that is sized to engage or mate with a corresponding opening on the exterior surface of the implant.

As seen in FIGS. 13 and 17, for example purposes, engagement element 218 is configured as a knob-like structure, although it is contemplated that other protrusion-like structures including, but not limited to spring balls, rods or pins may be used.

FIGS. 12 and 15 further show length control mechanism 300 that functions to engage with the implant and mechanically change the overall length of the implant both through extension of the implant and contraction or shortening of the implant. This is generally accomplished by using the rotary motion of length control mechanism 300 that mates with a corresponding length adjustment mechanism in the implant. The length adjustment mechanism of the implant is designed to convert the rotary motion of the length control mechanism 300 to translational motion, wherein the overall linear length of the implant is then changed. Length control mechanism 300 includes a gripping portion 301 that is positioned at the proximal end of surgical instrument 11. Gripping portion 301 is typically shaped as a knob or other similar structure to allow the operating surgeon easy manipulation. Gripping portion 301 is connected to the proximal end of drive shaft 303 that extends generally in a proximal to distal direction and is also substantially parallel to longitudinal axis 210.

As seen in FIG. 19, drive shaft 303 passes through hole 103 and is encased by cannulated tube 304 within handle assembly 100. Cannulated tube 304 is sized to allow drive shaft 303 to move in a distal to proximal direction and rotate. Attached to the distal end of drive shaft 303 is a gear assembly 302.

FIGS. 13, 15 and 17 show gear assembly 302 extending to a distance that is generally between arms 207, 208 that enables gear assembly 302 to enter through one of the several holes of the implant to engage the length adjustment mechanism of the implant. As seen in FIG. 13, gear assembly 302 is secured to the distal end of drive shaft 303 approximately proximate to the exit point of drive shaft 303 from cannulated tube 304. Because of the securement of gear assembly 302 directly to drive shaft 303, when gripping portion 301 is rotated clockwise, this directional motion is directly translated to gear assembly 302 that correspondingly rotates in a clockwise direction. It should be noted that length control mechanism 300 may be rotated both in a clockwise and counter-clockwise direction depending on whether the surgeon is lengthening (expanding) or shortening (contracting) the implant.

FIGS. 12, 15 and 19 generally exhibit locking mechanism 400. For example purposes, surgical instrument 11 as depicted in these figures includes two locking mechanisms 400, although it is contemplated that only one locking mechanism may be necessary for securing the overall length of the implant post-implantation. As seen in the cross-section view of FIG. 19, locking mechanism 400 has a gripping portion 401 that is positioned near the proximal end of surgical instrument 11 and proximate to handle assembly 100. Gripping portion 401 is typically configured as a knob or other handle-like shape to allow the operating surgeon easy grasping and manipulation when in use. Connected to gripping portion 401 is connecting rod 403 that extends in a proximal to distal direction and substantially parallel to longitudinal axis 210. Connecting rod 401 passes through hole 104 in handle assembly 100, with hole 104 being sized to allow for rotational and translational movement of connecting rod 403 without any impingement. Connected to the distal portion of connecting rod 403 is coupling end 402. (See FIG. 13.)

As seen in FIGS. 13, 16 and 18, connecting rod 403 may include transition portion 408 that may be slightly curved and fabricated from a flexible material to allow for curving of coupling end 402 and entry into alignment body 214. Examples of possible flexible materials to use to construct transition portion 408 include nitinol or other elastic/pseudoelastic metals and various compliant polymers, including but not limited to polyethylene and polystyrene. Coupling end 402 further includes a distal tip 406 that is configured to allow for detachably coupling of the locking pin/screw following securement within the implant. As seen in FIG. 17, distal tip 406 may be shaped as a hex or other geometric shape that would in turn match up with the head of the corresponding locking pin/screw.

FIGS. 13, 16 and 17 show further that connecting rod 403 may also include a bearing portion 407 that slidingly engages with a slot 219 that is positioned in the lateral side of alignment body 214. Slot 219 is generally sized to allow for rotational and translational movement of bearing portion 407 while also correctly aligning tip 406 with a hole in the side of the implant for the insertion of the locking pin/screw. Depending on whether there are one or two locking mechanisms 400 present in the invention will determine the number of slots 219 present in alignment body 214. Although not shown, it would be understood by one skilled in the art that the locking pin/screw may include external threads for engaging the side hole of the implant or the internal length adjustment mechanism. An alternative locking mechanism either on the head or engagement end of the locking pin/screw may be used to secure the locking pin/screw to the internal length adjustment mechanism of the implant.

As shown in FIG. 15, surgical instrument 11 may use two locking mechanisms 400. If this is the case, connecting rods 403 will generally run parallel to each over the length of surgical instrument 11. Having two locking mechanisms 400 present allows the operating surgeon to secure the implant at two locations to ensure long term stability of the overall length of the implant post-operatively.

The surgical technique for implantation of an implant 700 is well known in the art, including the appropriate surgical exposure and dissection techniques. The method generally includes, obtaining an implant 700 and surgical instrument 11 that may include handle assembly 100 positioned at the proximal end of surgical instrument 11, elongate member 201 having a first end 202 being located adjacent to handle assembly 100 and second end 203 connected to implant engagement assembly 204. Surgical instrument 11 may further have length control mechanism 300, which generally will be constructed of gripping portion 301, gear assembly 302 and drive shaft 303. Surgical instrument 11 may yet further have at least one locking mechanism 400 that has gripping portion 401, coupling end 402 and connecting rod 403. It should be understood that all of the above noted instrument components and respective elements include the same structural and functionality characteristics as described previously herein.

The method may further include the step of coupling implant 700 to implant engagement assembly 204, or more specifically engagement member 216. Implant 700 is grasped or held by surgical instrument 11 when the operating surgeon places implant 700 between engagement members 216. The operating surgeon then rotates either clockwise or counter-clockwise elongate member 201 via holding gripping portion 211 depending on whether arms 207, 208 need to be spread farther apart or brought closer together to make contact with implant 700. The operating surgeon may forego holding onto the gripping portion 211 and may also turn elongate member 201 along its shaft as well. Upon rotation of elongate member 201, external threads 212 engage internal threads 209 of actuation body 205 causing actuation body 205, depending on the direction of rotation of elongate member 201, to move either proximally or distally. Movement of actuation body 205 results in drive links 213 actuating arms 207, 208 to either move closer together to grasp the implant or farther apart to release the implant from between engagement members 216. The pivoting connection between arms 207, 208 and engagement member 216 allows holding portion 206 to accommodate and engage a wide range of sizes, configurations and diameters of implants.

Figure 20:
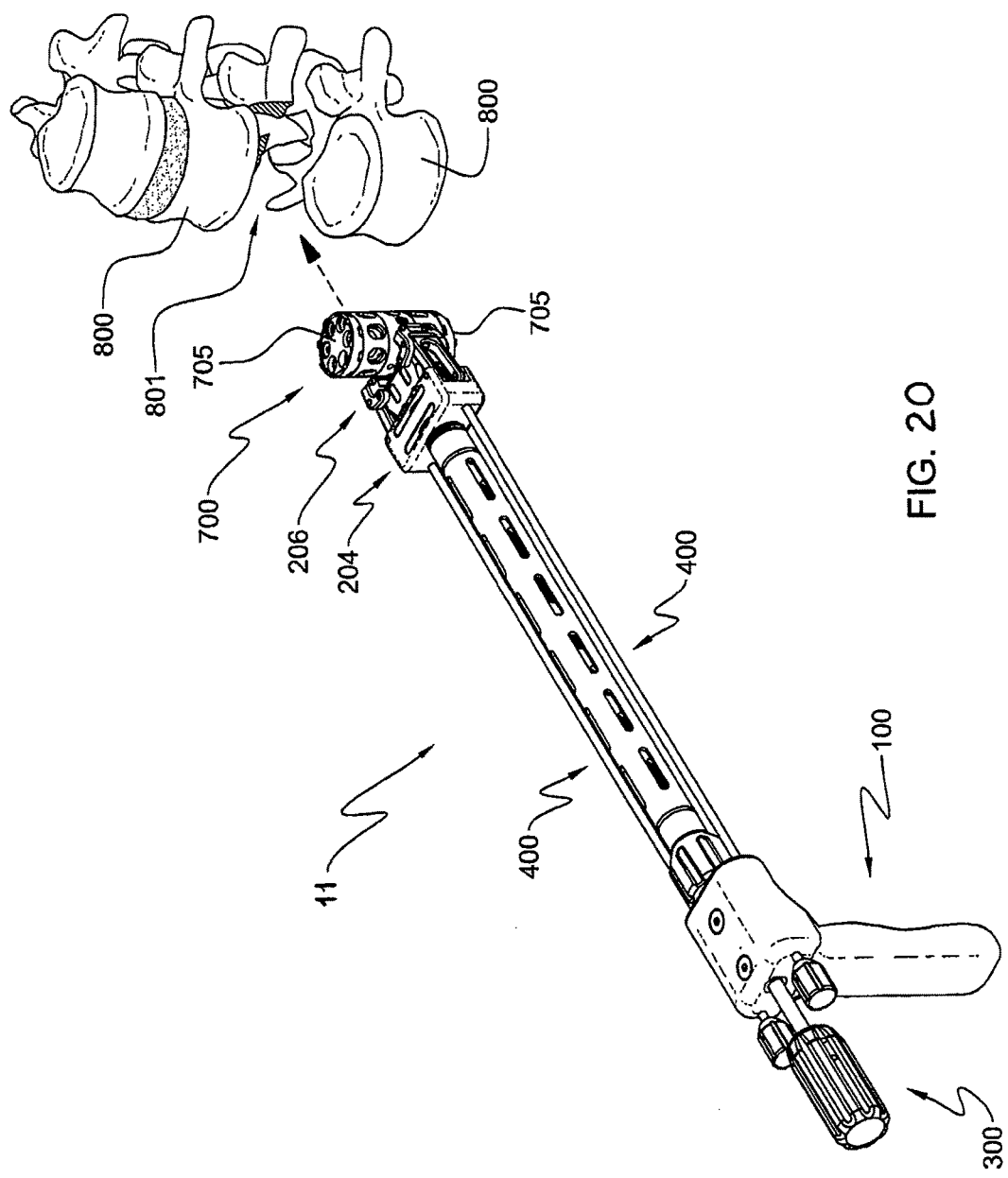
FIG. 20 is a perspective view of a spinal implant coupled to the surgical instrument of FIG. 12, shown positioned prior to insertion into a space between two vertebral bodies, in accordance with an aspect of the present invention.
Figure 25:
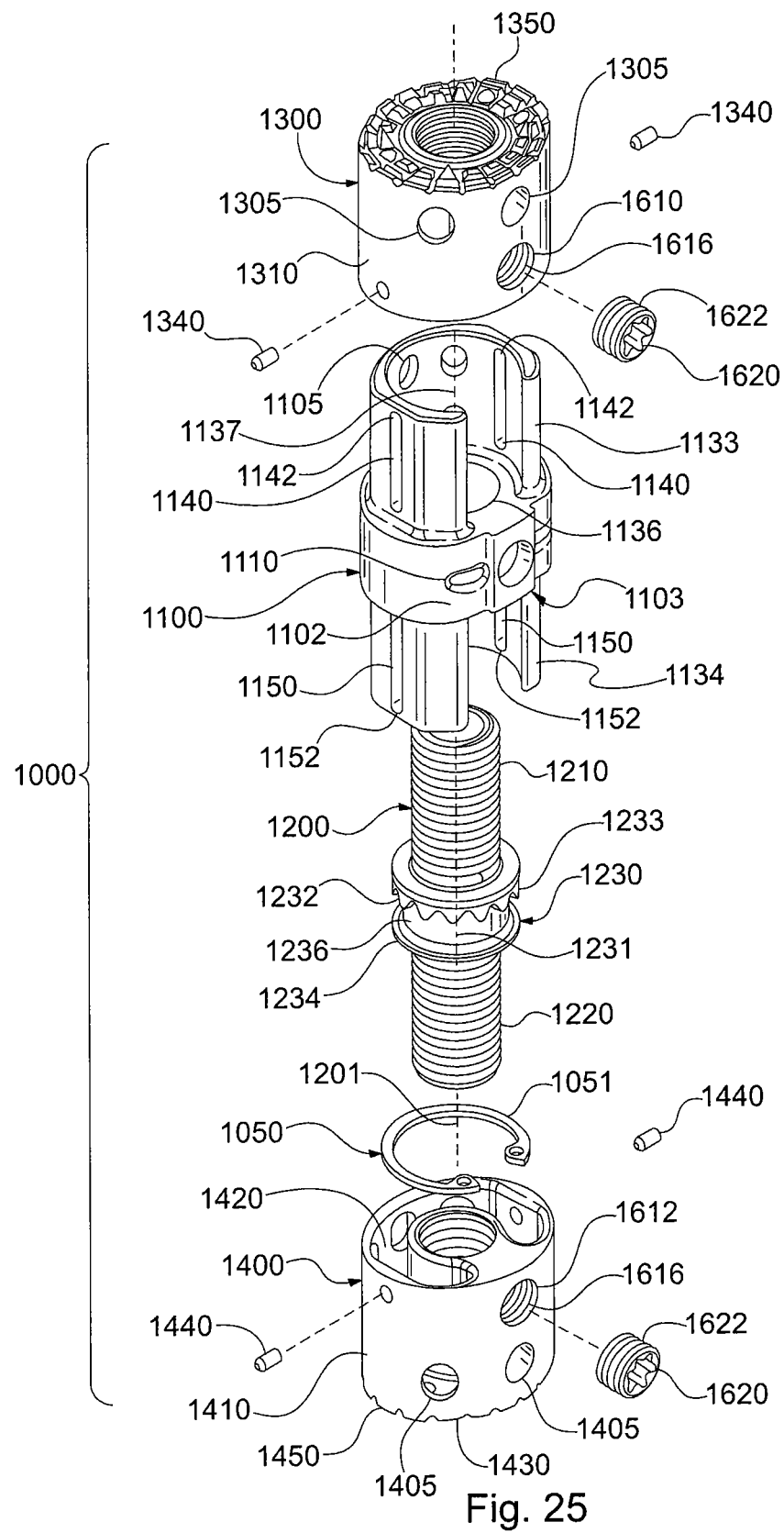
FIG. 25 is a perspective, exploded view of another embodiment of a vertebral body replacement device, in accordance with an aspect of the present invention.

As shown in FIG. 20, the surgical method may also include the steps of inserting surgical instrument 11 and the attached implant 700 through the skin opening and positioning the attached implant 700 adjacent to a space 801 between the two target bones 800. For example purposes only, as seen in FIG. 20, the two bones may be vertebral bodies or vertebrae 800.

FIGS. 21 and 22 exhibits a possible further step of the method, the extension or contraction of the overall length of implant 700 until the two ends 705 (Not Shown) of implant 700 make contact with vertebrae 800 resulting in a force being applied by implant 700 to maintain the space opening between the two vertebrae 800. The overall length of implant 700 may be extended or contracted (shortened) by rotating length control mechanism 300 either in a clockwise or counter-clockwise direction. Following the engagement of implant 700 with holding portion 206 of surgical instrument 11, the operating surgeon will push gripping portion 301 in a proximal direction resulting in drive shaft 303 and attached gear assembly 302 also moving proximally, with gear assembly 302 entering hole 702. Although not shown, gear assembly 302 will upon moving into the inner part of implant 700 engage a correspondingly configured length adjustment mechanism. Once gear assembly 302 is engaged with the length adjustment mechanism, the operating surgeon will turn gripping portion 301 either in a clockwise or counter-clockwise direction. When gripping portion 301 is rotated, drive shaft 303 and connected gear assembly 302 will also rotate. As described in the above-noted pending applications that have been incorporated herein by reference, length adjustment mechanism of implant is configured to convert the rotational movement of gear assembly 302 into translational movement within the implant. Essentially, when length control mechanism 300 is rotated in one direction implant 700 will extend or get longer and rotating length control mechanism 300 in the opposition direction will shorten or contract implant 700 while implant is placed between two bones. This novel functionality provides the operating surgeon with the ability to accurately adjust and ensure proper implant sizing without compromising positioning within the operative space.

FIGS. 22 and 23 show further the possible step of fixing or securing the overall length of implant 700 by the insertion of locking pins/screws 405 into holes 704 of implant 700 once the appropriate overall length has been determined. The operating surgeon uses locking mechanism 400 by initially coupling locking pins 405 to tips 406 (Not Shown). Following the final positioning and sizing of the implant in vivo, the operating surgeon will hold and turn gripping portion 401 that in turn rotates connecting rod 403. Depending on the locking or thread configuration of locking pin 405 and hole 704, gripping portion 401 may be turned either in a clockwise or counter-clockwise direction. Gripping portion 401 is then pushed in a proximal direction causing locking pin 405 to enter hole 704 and engage either threads or another securement configuration within implant 700. Following the rotational insertion of locking pin 405 into hole 704, the length adjustment mechanism will be locked in place, thereby fixing the overall length of implant 700. Once locking pin 405 is fully seated, the operating surgeon will move locking mechanism 400 in a distal direction and uncouple tip 406 from locking pin 405.

It should be understood by those skilled in the art that the surgical method and use of surgical instrument 11 described herein may be performed using either anterior, posterior or lateral approaches to the example spinal column. In addition, an operating surgeon may use a minimally invasive surgical approach and employ surgical instrument 11 because of the multi-functionality (i.e., grasp, extend/contract and lock) operation of surgical instrument 11 relative to implant 700. It is further contemplated that surgical instrument 11 may be sized to allow for endoscopic insertion. Having these multiple functions incorporated into one instrument addresses a long felt need of providing the operating surgeon with the ability to keep one instrument in the wound and to not have to repeatedly remove the instrument and replace it with a different instrument to perform another function. Having a multi-purpose surgical instrument will lessen the potential for tissue disruption and adjacent structural damage.

It is further contemplated that a method of fabricating surgical instrument 11 may include the steps of providing handle assembly 100 with an additional step of providing elongate member 201 with one end 202 of the elongate member 201 being positioned adjacent to handle assembly 100 and second end 203 of elongate member 201 being moveably or threadingly connected to implant engagement assembly 204. Rotational movement of elongate member 201 relative to handle assembly 100 and implant engagement assembly results in the grasping and holding of the implant between engagement members 216.

The fabrication method may also include the further step of providing a length control mechanism 300 that typically allows the operating surgeon to adjust the overall length of the implant while holding the implant in place between engagement members 216. Yet a further step of the method may include providing at least one locking mechanism 400 for the surgical instrument 11. Locking mechanism 400 permits the operating surgeon with the ability to secure and fix the overall length of the implant after the final positioning and sizing is accomplished in vivo.

It is further contemplated that a spinal implant insertion kit comprised of various cross-sectional sizes, cross-sectional polygonal and circular/oval shapes and longitudinal lengths of implants and a corresponding surgical instrument 11 will be available as a kit. This will allow the operating surgeon to pick and choose these modular components that are necessary to assemble a spinal implant that best fits into a certain spinal segment or to address a certain anatomical deformity presented in a patient. The kit would further include a single inserter 11 that may be used with the multiple sized (both length and diameter) spinal implants. It is also contemplated that multiple sized inserters may be included in the kit to accommodate the various anatomic regions of the spine and the corresponding implant sizes (i.e., lumbar, thoracic and cervical). Inserter 11 includes handle assembly 100, elongate member 201, length control mechanism 300 and at least one locking mechanism 400. For brevity sake, all of the above noted inserter components and respective elements will not be discussed again here and include the same structural and functionality characteristics as described previously herein.

Referring now to FIGS. 25-36, a vertebral body replacement device 1000 in accordance with another exemplary embodiment of the invention is shown. Vertebral body replacement device 1000 includes a body member 1100, a central rod member 1200, a first end member 1300 and a second end member 1400. Those skilled in the art will observe that body member 1100, central body member 1200, first end member 1300 and second end member 1400 have features that correspond to features shown and described above with reference to device 10. Therefore, the descriptions of corresponding components and features on device 10 are incorporated by reference into this section.

As with device 10, body member 1100 has an inner wall 1101 and an outer wall 1102. Outer wall 1102 features a plurality of tool ports 1103 that extend from outer wall 1102 through inner wall 1101. The plurality of tool ports 1103 are arranged along a portion of the perimeter 1110 of body member 1100. Outer wall 1102 is configured for engagement with a tool, such as a driver tool operable to expand vertebral body device 1000. First end member 1300 and second end member 1400 each have end walls 1350 and 1450, respectively. End walls 1350 and 1450 each feature projections or spikes 1352 and 1452, respectively. Projections 1352 and 1452 are configured to engage a vertebral body when vertebral body replacement device 1000 is fully expanded, or almost fully expanded, in a space between two vertebrae. Body member 1100 may be available to the operating surgeon in various outside diameter sizes and longitudinal lengths, like body member 30.

Central rod member 1200 includes a first threaded portion 1210 and a second threaded portion 1220. Central rod member 1200 is configured to be operatively associated within body member 1100, and includes a gear wheel portion 1230. Gear wheel portion 1230 includes a toothed surface 1232 and a support surface 1234. Toothed surface 1232 includes a circular arrangement of gear teeth 1233 that surround central rod member 1200. Support surface 1234 is separated from toothed surface 1232 by a recessed section 1236.

Figure 26:
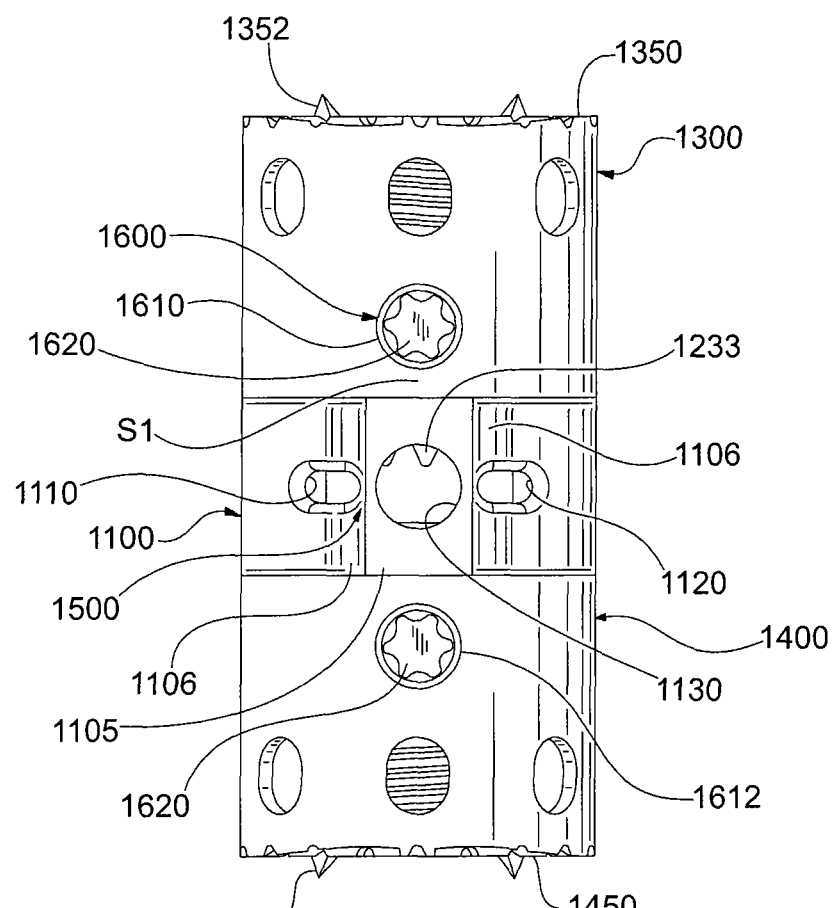
FIG. 26 is a front view of the vertebral body replacement device of FIG. 25 in accordance with an aspect of the present invention.
Figure 27:
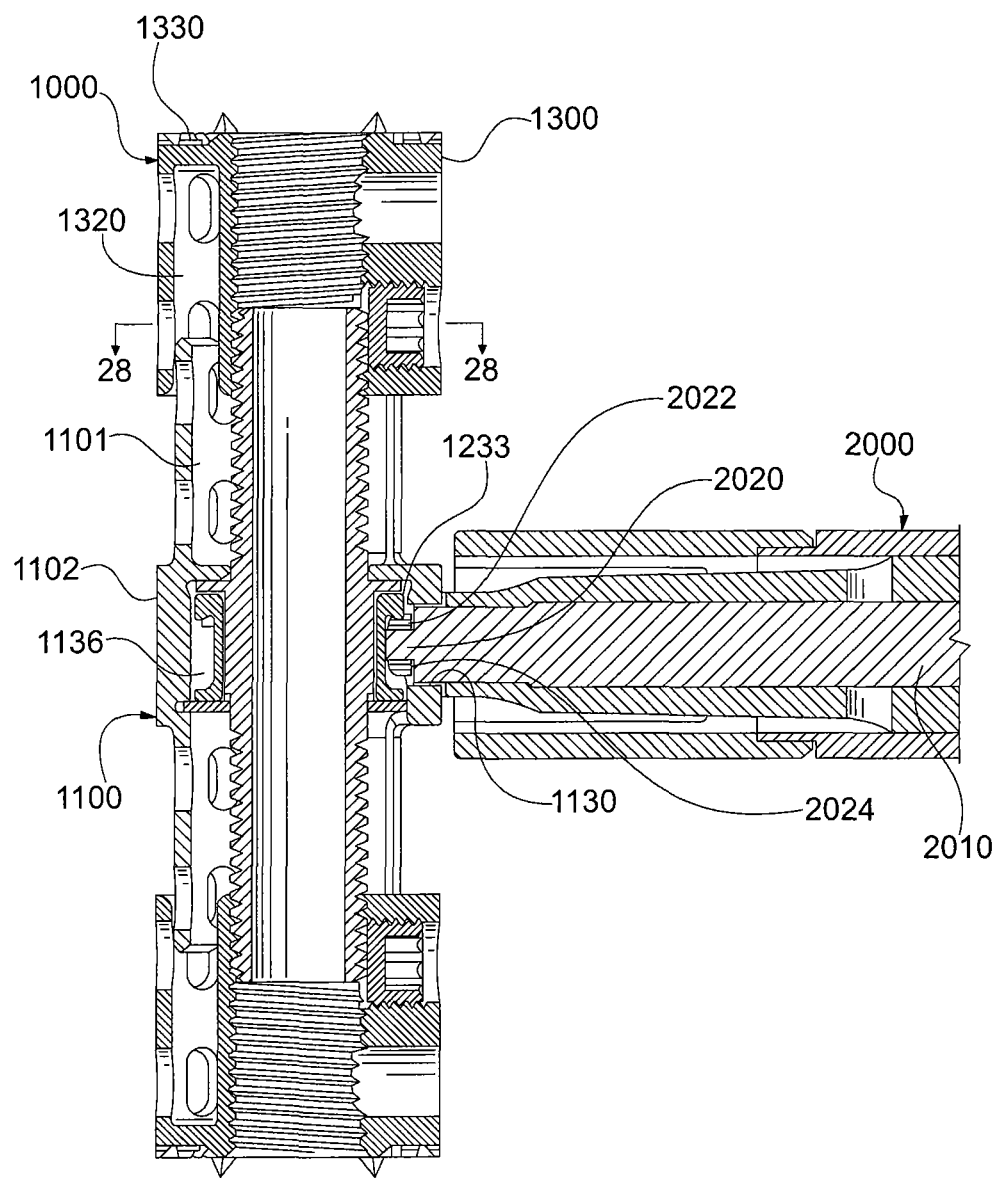
FIG. 27 is a cross-sectional, side elevational view of the vertebral body replacement device of FIG. 25 in accordance with an aspect of the invention, shown with an insertion instrument in accordance with an aspect of the invention.
Figure 30:
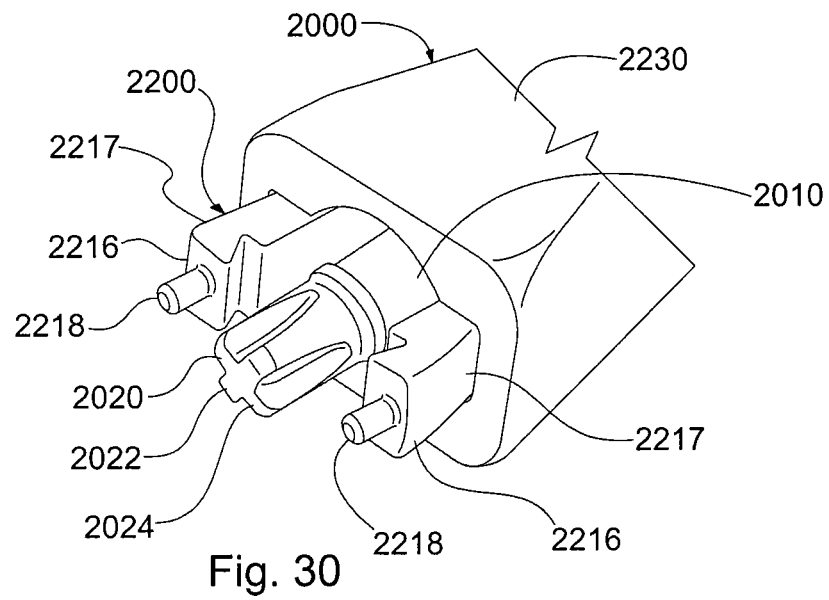
FIG. 30 is an enlarged perspective view of a distal end portion of the insertion instrument of FIG. 29 in accordance with an aspect of the invention.

The plurality of tool ports 1103 on body member 1100 includes a first tool port 1110, a second tool port 1120 and a third tool port 1130. Third tool port 1130 is positioned between first tool port 1110 and second tool port 1120. Gear teeth 1233 of gear wheel portion 1230 are exposed through third tool port 1130 when central rod member 1200 is operatively associated within the body member, as shown in FIG. 26. Third tool port 1130 is configured to receive a drive shaft 2010 of a surgical instrument 2000, as shown in FIGS. 27 and 30. Drive shaft 2010 has a distal end 2020 that includes a gear mechanism 2022. Gear mechanism 2022 includes a plurality of teeth 2024 that are individually configured to fit between adjacent teeth 1233 on toothed surface 1232. When drive shaft 2010 is inserted through third tool port 1130, and when gear mechanism 2022 is engaged with toothed surface 1232, vertebral body replacement device 1000 can be expanded or retracted in response to rotation of the drive shaft.

Body member 1100 includes a first or superiorly positioned end receptacle 1133 and a second or inferiorly positioned end receptacle 1134. A longitudinal axis 1137 extends between end receptacles 1133 and 1134. A middle chamber 1136 extends between first end receptacle 1133 and second end receptacle 1134. First tool port 1110, second tool port 1120 and third tool port 1130 all extend through outer wall 1102 and into middle chamber 1136.

First end member 1300 is configured to threadingly engage first threaded portion 1210 of central rod member 1200. Similarly, second end member 1400 is configured to threadingly engage second threaded portion 1220 of central rod member 1200. As will be described in more detail below, body member 1100, first end member 1300 and second end member 1400 include features that inhibit rotational movement of the first and second end members relative to the body member when central rod member 1200 is rotationally actuated to move the first end member and the second end member in an axial direction relative to the body member.

Proper engagement between drive shaft 2010 and toothed surface 1232 allows vertebral body replacement device 1000 to be expanded with minimal mechanical resistance or jamming of parts. Should the surgeon experience excessive mechanical resistance upon rotating the drive shaft 2010, this resistance can interfere with the surgeon's ability to sense, by tactile feel, when vertebral body replacement device 1000 is completely expanded. Resistance can be caused by improper positioning of the drive shaft 2010 relative to toothed surface 1232. Although the relative position of drive shaft 2010 can be controlled by controlling the shape and size of the tool port that receives the drive shaft, a certain amount of clearance between the drive shaft 2010 and edge of the tool port must be provided to facilitate insertion of the drive shaft. If the axial position of the drive shaft 2010 is not firmly secured, the clearance can allow the drive shaft 2010 to move slightly after it is inserted through the tool port. Any such movement can cause the drive shaft 2010 to move out of proper engagement with toothed surface 1232, leading to an improper engagement and mechanical resistance.

To reduce or prevent the potential for mechanical resistance caused by misalignment between the drive shaft and toothed surface, vertebral body replacement devices in accordance with the invention preferably include an alignment and indexing mechanism. The alignment and indexing mechanism ensures that the teeth on the drive shaft are properly indexed and engaged with the gear teeth on the toothed surface after the drive shaft is inserted through a tool port. The alignment and indexing mechanism also ensures that the teeth on the drive shaft remain properly indexed and engaged with the gear teeth on the toothed surface. This is accomplished by providing one or more engagement points on the outer wall of the vertebral body. The engagement point or points are located and configured to mate and lock with engagement elements on a surgical instrument, only when the surgical instrument and drive shaft are positioned in the correct location to properly engage the toothed surface.

FIG. 26 shows an alignment and indexing mechanism 1500 in accordance with one exemplary embodiment of the invention. Alignment and indexing mechanism 1500 is formed by the first tool port 1110 and the second tool port 1120. First and second tool ports 1110 and 1120 are positioned on opposite sides of third tool port 1130, and are equidistant from the first and second end members 1300 and 1400. Each of the first and second tool ports 1110 and 1120 have an elongated configuration and is configured to cooperate with a corresponding alignment and indexing feature on the surgical instrument 2000.

Figure 29:
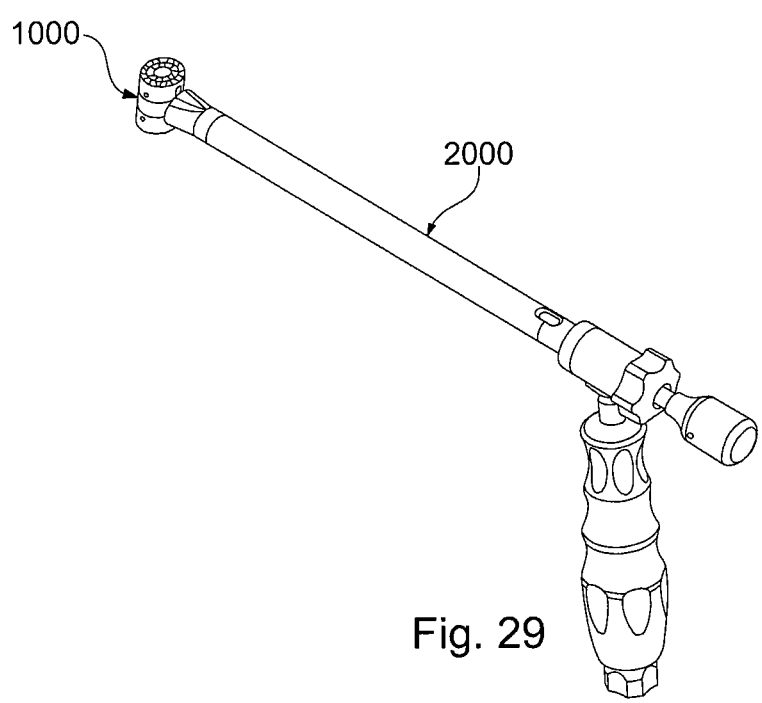
FIG. 29 is a perspective view of the vertebral body replacement device of FIG. 25 in accordance with an aspect of the invention, shown with an insertion instrument in accordance with an aspect of the invention.
Figure 31:
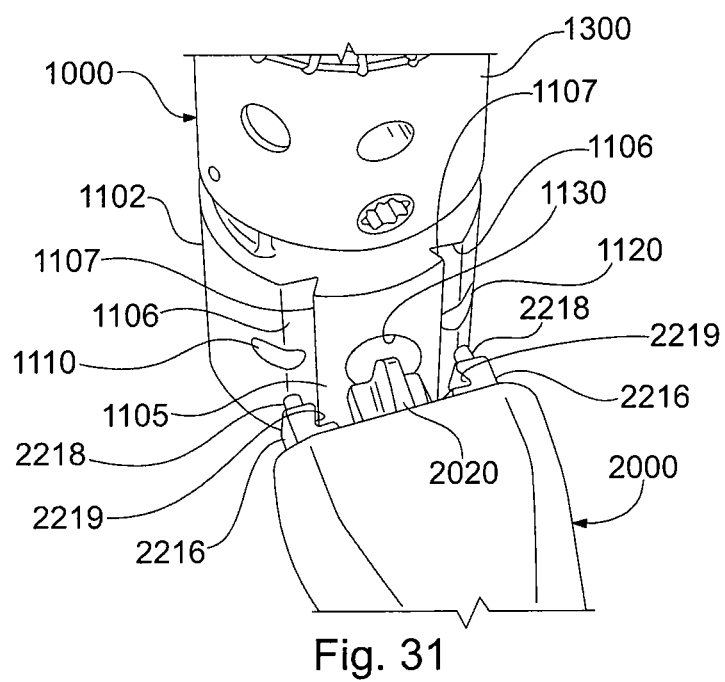
FIG. 31 is another enlarged perspective view of a distal end portion of the insertion instrument of FIG. 29 in accordance with an aspect of the invention, shown with the vertebral body replacement device of FIG. 25.

Referring now to FIGS. 29-31, surgical instrument 2000 includes an alignment and indexing feature 2200 that includes two engagement members 2216. Engagement members 2216 are similar in many respects to engagement members 216 described above, insofar as both sets of engagement members can be moved toward one another to grasp an implant. Each engagement member 2216 includes an engagement element in the form of a pin 2218. A sleeve 2230 surrounds engagement members 2216, engaging an outer edge 2217 of each engagement member. Engagement members 2216 are axially displaceable relative to sleeve 2230 in a proximal direction, in which the engagement members are drawn into the sleeve, and a distal direction, in which the engagement members are extended out of the sleeve. As such, engagement members 2216 move inwardly toward one another and converge together in response to being drawn proximally into sleeve 2230, and move outwardly and away from one another in response to being extended distally out of the sleeve. Engagement members 2216 are movable toward one another until they reach a position in which pins 2218 are located in a clamping position. Engagement members 2216 can be displaced away from one another to spread pins 2218 apart until the pins reach a release position.

First and second ports 1110 and 1120 are positioned to receive engagement pins 2218 on instrument 2000. The elongated geometry of first and second ports 1110 and 1120 are such that pins 2218 can reside in the first and second ports when the pins are in either the clamping position or a release position. Each pin 2218 is centered between top and bottom edges of one of the first and second ports 1110 and 1120. This sets the proper orientation and position of drive shaft 2010 so that gear mechanism 2022 of the drive shaft properly engages the toothed surface of gear wheel portion 1230. In particular, first and second slots 1110 and 1120 control the position of drive shaft 2010 as it is inserted through third tool port 1130, so that teeth 2024 are at the precise position and orientation required to index with and fit between teeth 1233 on toothed surface 1232. This ensures proper engagement between drive shaft 2010 and gear wheel portion 2130 with minimal mechanical resistance. Pins 2218 also make it easier to re-attach instrument 2000 to implant 1000 in the event that the instrument is disconnected from the implant during insertion. Ordinarily, it can be very difficult to navigate a driver instrument into an incision and realign the instrument's driver tip in situ with the gear mechanism in the implant. Pins 2218 and first and second ports 1110 and 1120 make reconnection much simpler, because the engagement of the pins with the first and second ports sets the proper orientation for the drive shaft.

Engagement between vertebral body replacement device 1000 and surgical instrument 2000 is enhanced by a "dovetail" projection 1105 on outer wall 1102. Dovetail projection 1105 is formed by a pair of parallel channels 1106 in outer wall 1102. Each channel 1106 has a V-shaped cross-sectional profile and forms a pointed edge 1107 on each side of dovetail projection 1105. Engagement members 2216 have V-shaped notches 2219 that geometrically conform to pointed edges 1107. When engagement members 2216 are moved toward the clamping position, V-shaped notches 2219 lockingly engage pointed edges 1107. In this condition, vertebral body replacement device 1000 is securely gripped by instrument 2000 with drive shaft 2010 positioned to properly engage the toothed surface. The secure engagement prevents drive shaft from shifting or slipping out of this position, ensuring that proper indexing and engagement are maintained.

Referring again to FIGS. 25 and 26, vertebral body replacement device 1000 includes a locking mechanism 1600 to fix the position of the implant after it is expanded to a desired height. Locking mechanism 1600 includes a pair of tool ports in the form of locking pin holes 1610 and 1612. Locking pin holes 1610 and 1612 are similar to locking pin hole 71 discussed above. Locking pin hole 1610 is formed in first end member 1300 at a location that is superior to third tool port 1130. Locking pin hole 1612 is formed in second end member 1400 at a location that is inferior to third tool port 1130. Each locking pin hole 1610 and 1612 contains a locking element in the form of a threaded locking pin or screw 1620. Each locking pin 1620 has an outer thread 1622 that engages an inner thread 1616 inside each of the locking pin holes 1610 and 1612.

Figure 28:
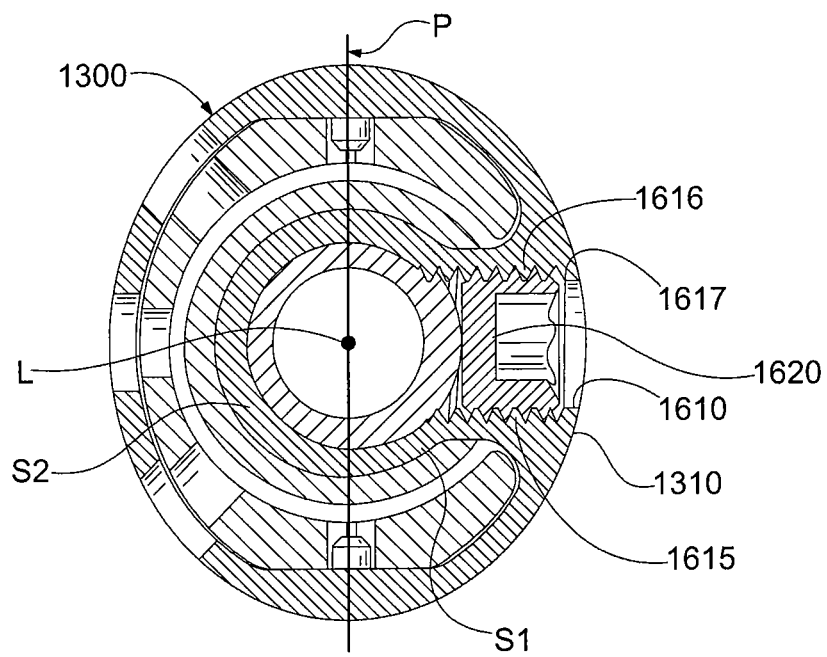
FIG. 28 is a cross-sectional, plan view of the vertebral body replacement device of FIG. 25 in accordance with an aspect of the invention, taken through line 28-28 of FIG. 27.

First end member 1300 includes an outer wall 1310, and second end member 1400 includes an outer wall 1410. The interior of first end member 1300 is preferably identical or substantially identical to the interior of second end member 1400. For brevity, the interior of first end member 1300 will be described, with the understanding that the features inside first end member 1300 are also present inside second end member 1400. Referring to FIG. 28, the interior of first end member 1300 is shown. Inner thread 1616 extends along an inner wall 1615 of locking pin hole 1610 and terminates at a terminal point 1617. Terminal point 1617 is recessed inside and spaced from outer wall 1310. Locking pin 1620 is confined to locking pin hole 1610 and cannot be advanced past terminal point 1617. As such, locking pin 1620 cannot be removed from locking pin hole 1610 through outer wall 1310.

Figure 32:
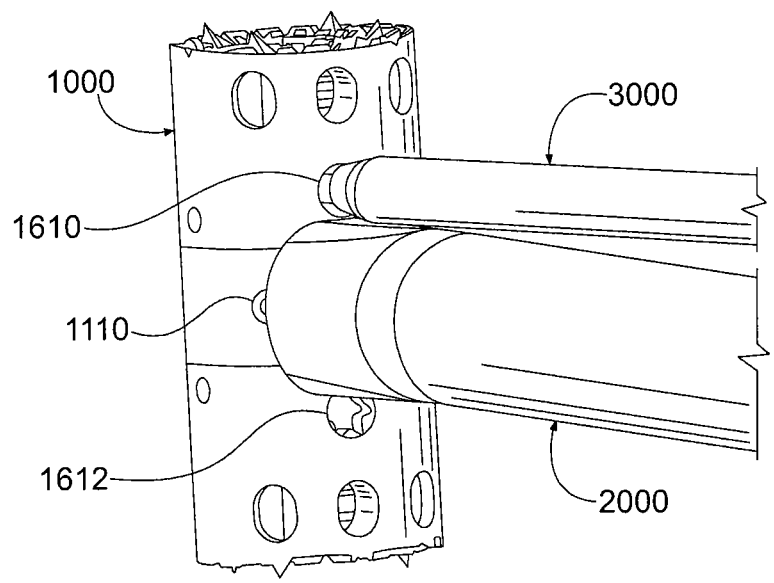
FIG. 32 is another enlarged perspective view of a distal end portion of the insertion instrument of FIG. 29 in accordance with an aspect of the invention, shown with the vertebral body replacement device of FIG. 25 and a tool in accordance with an aspect of the invention.

First tool port 1110, second tool port 1120, third tool port 1130, locking pin hole 1610 and locking pin hole 1620 are located in close proximity to one another on the same side or "segment" of the implant. The term "segment", as used herein, means a section of the implant that is defined when a plane is passed through the implant parallel to and in coincidence with the implant's longitudinal axis. The term "longitudinal axis", as used herein, means the axis that extends through a center point of each end wall of the implant. FIG. 28 shows a plane P passing through longitudinal axis L of implant 1000, defining two segments S1 and S2. First tool port 1110, second tool port 1120, third tool port 1130, locking pin hole 1610 and locking pin hole 1620 are all located in close proximity to one another in segment S1, seen best in FIG. 26. The close arrangement of the tool ports and locking pin holes on the same segment allows different instruments to engage the implant from the same approach angle. FIG. 32 shows surgical instrument 2000 engaging first tool port 1110, second tool port 1120 and third tool port 1130 (the second and third tool ports being behind the instrument and not visible in the Figure). A separate driver instrument 3000 is shown being inserted into locking pin hole 1610 to engage one of the locking pins 1620.

Referring back to FIG. 25, vertebral body replacement device 1000 includes a C-shaped support ring 1050. Support ring 1050 has a bearing surface 1051 that contacts central rod member 1200 when the central rod member is operatively positioned within body member 1100. Support surface 1234 of gear wheel portion 1230 is configured to contact bearing surface 1051 of support ring 1050 when central rod member 1200 is operatively positioned within the body member. Central rod member 1200 has a central axis 1201 extending between first threaded portion 1210 and second threaded portion 1220. Gear wheel portion 1230 has a rotational axis 1231 that is substantially coaxial to central axis 1201. In this arrangement, as gear wheel portion 1230 is rotated about rotational axis 1231, first and second threaded portions 1210 and 1220 correspondingly rotate about central axis 1201.

First end member 1300 includes an internal wall 1320, an end wall 1330, and a travel limiting mechanism in the form of a pair of pins 1340. Similarly, second end member 1400 includes an internal wall 1420, an end wall 1430 and a travel limiting mechanism in the form of a pair of pins 1440. First end member 1300 has a pair of pin holes 1341 for receiving pins 1340, and second end member 1400 has a pair of pin holes 1441 for receiving pins 1440. Body member 1100 includes a first pair of longitudinal slots 1140 adapted to receive pins 1340 and a second pair of longitudinal slots 1150 adapted to receive pins 1440. Pins 1340 and 1440 align with and engage first and second longitudinal slots 1140 and 1150 when the implant components are assembled. The engagement of pins 1340 with the first longitudinal slots 1140 prevents first end member 1300 from rotating relative to body member 1100. Similarly, the engagement of pins 1440 with second longitudinal slots 1150 prevents second end member 1300 from rotating relative to body member 1100. First longitudinal slots 1140 have terminal ends 1142 that limit how far pins 1340 can travel, and second longitudinal slots 1150 have terminal ends 1152 that limit how far pins 1440 can travel. In this arrangement, pins 1340 and 1440, in combination with first and second longitudinal slots 1140 and 1150, limit how far the first and second end members can be expanded relative to body member 1100.

First and second end members in accordance with the invention may include one or more holes disposed in at least one of the external wall and the end wall and extending therethrough to allow for the placement of bio-compatible material within the first and second end members. Body members in accordance with the invention also may include one or more holes for receiving compatible material within the body members. For example, first end member 1300 includes multiple tool ports 1305, and second end member 1400 includes multiple tool ports 1405. Body member 1100 also includes multiple tool ports 1105. Tool ports 1305, 1405 and 1105 are configured and positioned to receive bone graft and other bio-compatible material into various areas inside the implant. Tool ports 1305, 1405 and 1105 are also configured to receive impactor tools to pack in bone graft material within the spaces inside implant 1000.

Referring now to FIGS. 33-36, a vertebral body replacement device 5000 is shown in accordance with another exemplary embodiment of the invention. Vertebral body replacement device 5000 is similar in many respects to device 1000, but features a modular first end member 5300 and a modular second end member 5400 that attach to footplates 5500. First and second end members 5300 and 5400 cooperate with a body member 5100 and a central rod member 5200.

Figure 35:
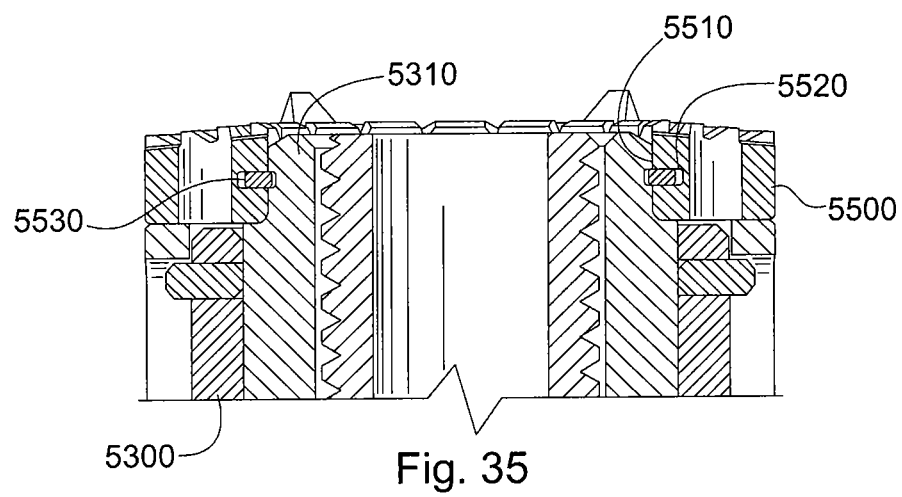
FIG. 35 is an enlarged truncated view of a the vertebral body replacement device of FIG. 33, showing one end member with a footplate member attached.

First end member 5300 and second end member 5400 are identically configured. Therefore, only first end member 5300 will be described with the understanding that the features of first end member 5300 are also present on second end member 5400. Referring to FIG. 35, footplate 5500 is shown detachably coupled to first end member 5300. First end member 5300 includes a circular projection 5310 with an annular groove 5320. Each footplate 5500 has a central opening 5510 and an inner slot 5520 that carries an elastically deformable snap ring 5530. To attach footplate 5500 to first end member 5300, the footplate is placed over the first end member and pushed downwardly onto circular projection 5310 so that the circular projection extends into central opening 5510. As footplate 5500 is pushed down onto first end member 5300, snap ring 5530 expands radially outwardly in response to contact with the exterior of circular projection 5310, and remains in an expanded condition in which it slides over the exterior of the circular projection. In the expanded condition, snap ring 5530 maintains stored energy until the snap ring aligns with annular groove 5320. Once snap ring 5530 aligns with annular groove 5320, the snap ring is released from the expanded condition and retracts into the groove toward a more relaxed state. In this position, snap ring 5530 extends in both annular groove 5320 and slot 5520 to detachably couple footplate 5500 to first end member 5300.

Figure 33:
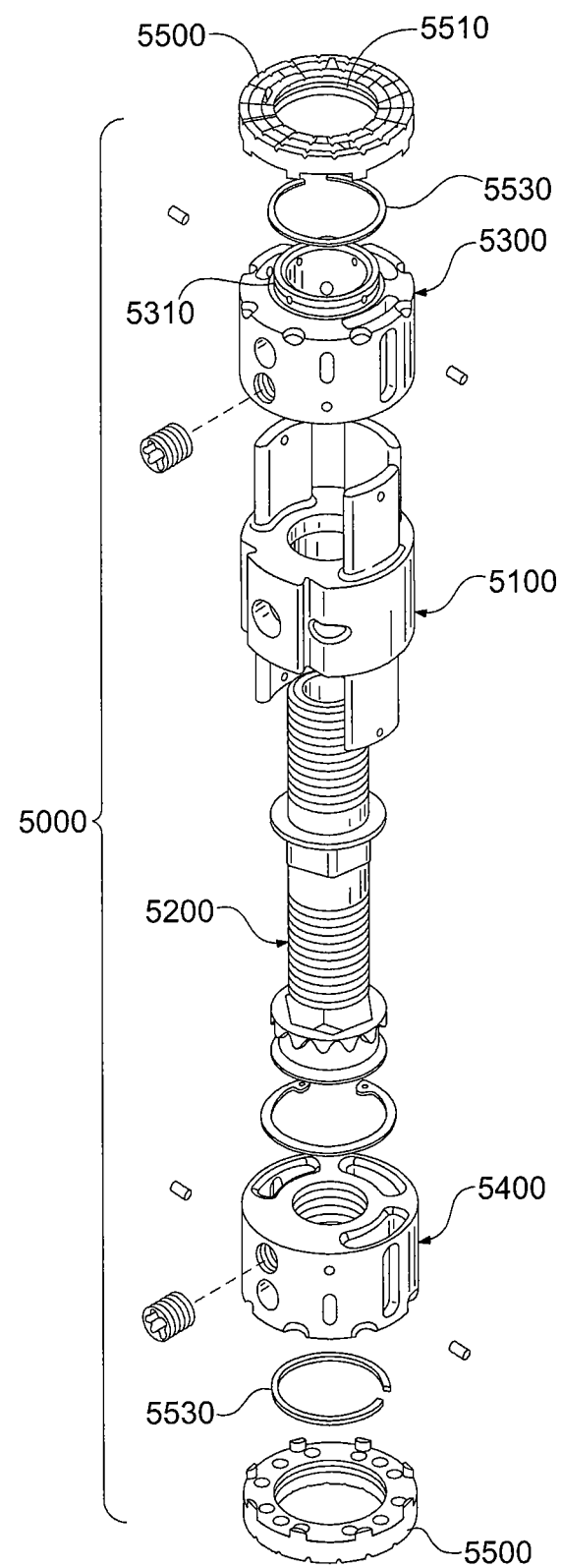
FIG. 33 is a perspective, exploded view of another embodiment of a vertebral body replacement device, in accordance with an aspect of the present invention.
Figure 34:
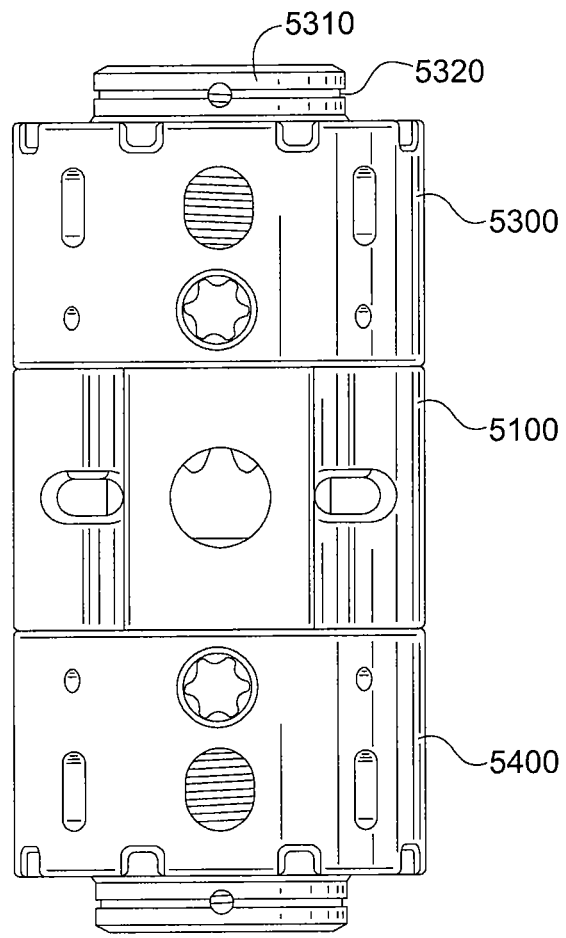
FIG. 34 is a front view of the vertebral body replacement device of FIG. 33 in accordance with an aspect of the present invention, with the end members shown without footplate members attached.
Figure 36:
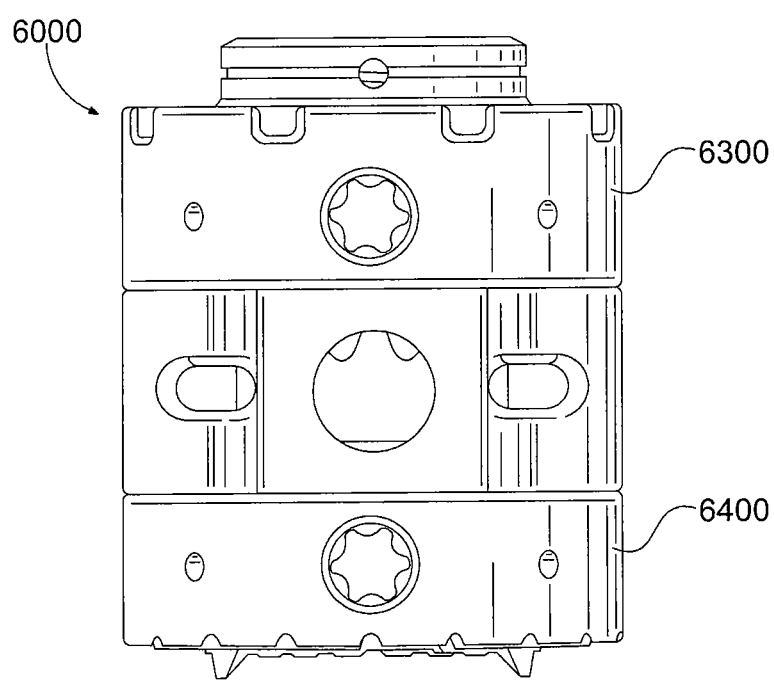
FIG. 36 is a front view of another embodiment of a vertebral body replacement device, in accordance with an aspect of the present invention.

The first and second end members 5300 and 5400 in FIG. 33 are modular, as noted above, in that they can connect with footplates, like footplates 5500. In contrast, first and second end members 1300 and 1400 in FIG. 25 have a "unitary" design. That is, they have end walls that directly engage vertebrae, and do not connect to footplates. It will be apparent to those skilled in the relevant art that various modifications, additions and substitutions can be made to these features and other features in accordance with the invention. With regard to the end members, vertebral body replacement devices in accordance with the invention need not have first and second end members that are identically configured. FIG. 36 shows a vertebral body replacement device 6000 in accordance with another embodiment of the invention that features different end member configurations. The first end member 6300 is modular, while the second end member 6400 is unitary.

Although the detailed description and drawing figures describe and show specific embodiments, it will be apparent to those skilled in the relevant art that various modifications, additions and substitutions can be made without departing from scope of the invention. Any such modifications, additions and substitutions are therefore to be considered within the scope of the following claims.

What is claimed is:

1. A vertebral body replacement device having a longitudinal axis and comprising:
   A. a central member having a threaded portion;
   B. a first end member comprising an end wall and a plurality of screw holes extending through the end wall of the first end member, the plurality of screw holes of the first end member comprising at least a first screw hole and a second screw hole, the plurality of screw holes radially arranged about a center point of the first end member, with a distance between the center point and the first screw hole defined by a first radius, and a distance between the center point and the second screw hole defined by a second radius, the first radius and the second radius extending within a plane substantially perpendicular to the longitudinal axis, with the second radius being separated from the first radius by an angle less than 180 degrees;
   C. a second end member comprising an end wall and at least one screw hole extending through the end wall of the second end member;
   D. a first footplate member comprising a first end surface having at least one aperture in the first end surface for attaching the first footplate member to the first end member;
   E. a second footplate member comprising a second end surface having at least one aperture in the second end surface for attaching the second footplate member to the second end member; and
   F. at least one locking screw for detachably connecting the first footplate member to the first end member,
   the first end member being axially displaceable relative to the second end member in response to rotational motion of the central member relative to the first end member and the second end member, so as to adjust an overall length of the vertebral body replacement device, and
   the first footplate member being detachably connected to the first end member in a desired orientation by inserting the at least one locking screw through the at least one aperture of the first footplate member and into one of the plurality of screw holes of the first end member,
   wherein, when the at least one aperture of the first footplate member is aligned with the first screw hole of the first end member, the at least one locking screw is insertible through the at least one aperture and into the first screw hole to attach the first footplate member to the first end member in a first orientation relative to the first end member, and
   wherein, when the at least one aperture of the first footplate member is aligned with the second screw hole of the first end member, the at least one locking screw is insertible through the at least one aperture and into the second screw hole to attach the first footplate member to the first end member in a second orientation relative to the first end member, the second orientation differing from the first orientation by said angle less than 180 degrees.

2. The vertebral body replacement device of claim 1, wherein the device defines a locking pin hole for receiving a threaded pin configured to lock the axial position of the first end member relative to the axial position of the second end member and fix the overall length of the device.

3. The vertebral body replacement device of claim 1, wherein the central member comprises a gear wheel portion having a tooth faced surface.

4. The vertebral body replacement device of claim 3, wherein the tooth-faced surface is arranged on a plane that is substantially perpendicular to the longitudinal axis of the vertebral body replacement device.

5. The vertebral body replacement device of claim 1, wherein the at least one locking screw comprises a plurality of locking screws for detachably connecting the first footplate member to the first end member.

6. The vertebral body replacement device of claim 1, wherein the first footplate member has a circular outer profile shape.

7. The vertebral body replacement device of claim 1, wherein the first footplate member has a non-circular outer profile shape.

8. The vertebral body replacement device of claim 1, wherein the first footplate member comprises at least one projection extending from the first end surface of the first footplate member.

9. The vertebral body replacement device of claim 8, wherein the at least one projection comprises a tooth-like projection.

10. The vertebral body replacement device of claim 1, wherein the first footplate member comprises a sidewall.

11. The vertebral body replacement device of claim 1, wherein the first end surface of the first footplate member is angled relative to the sidewall by an angulation Δ of 0°.

12. The vertebral body replacement device of claim 1, wherein the first end surface of the first footplate member is angled relative to the sidewall by an angulation Δ of between 0° and 20°.

13. The vertebral body replacement device of claim 1, further comprising a plurality of optional footplate members, each optional footplate member being interchangeable with the first footplate member or the second footplate member.

14. The vertebral body replacement device of claim 13, wherein the plurality of optional footplate members vary in outer profile shape.

15. The vertebral body replacement device of claim 13, wherein each optional footplate member comprises an end surface and a sidewall, said end surface being angled relative to said sidewall by an angulation Δ, the plurality of optional footplate members each having a different angulation Δ.

16. The vertebral body replacement device of claim 15, wherein the plurality of optional footplate members comprise a wide range of incrementally angled footplate members having an angulation Δ of between 0° and 20°.

17. The vertebral body replacement device of claim 1, wherein the plurality of screw holes in the end wall of the first end member further comprises a third screw hole.

18. The vertebral body replacement device of claim 17, wherein the plurality of screw holes are arranged uniformly around the longitudinal axis of the vertebral body replacement device.

19. The vertebral body replacement device of claim 1, wherein said angle less than 180 degrees is less than 90 degrees.

20. A vertebral body replacement device having a longitudinal axis and comprising:
    A. a central member having a threaded portion;
    B. a first end member comprising an end wall and a plurality of screw holes extending through the end wall of the first end member, the plurality of screw holes of the first end member comprising at least a first screw hole and a second screw hole, the plurality of screw holes radially arranged about a center point, with a distance between the center point and the first screw hole defined by a first radius, and a distance between the center point and the second screw hole defined by a second radius, the first radius and the second radius extending within a plane substantially perpendicular to the longitudinal axis, with the second radius being separated from the first radius by an angle less than 180 degrees;

C. a footplate member for directly engaging a first vertebral body, the footplate member comprising an end surface having at least one aperture arranged on the end surface for attaching the footplate member to the first end member;

D. at least one locking screw for detachably connecting the footplate member to the first end member; and E. a second end member for directly engaging a second vertebral body, the first end member being axially displaceable relative to the second end member in response to rotational motion of the central member relative to the first end member and the second end member, so as to adjust an overall length of the vertebral body replacement device, and the footplate member being detachably connected to the first end member in a desired orientation by inserting the at least one locking screw through the at least one aperture of the footplate member and into one of the plurality of screw holes of the first end member, wherein, when the at least one aperture of the footplate member is aligned with the first screw hole of the first end member, the at least one locking screw is insertible through the at least one aperture and into the first screw hole to attach the footplate member to the first end member in a first orientation relative to the first end member, and wherein, when the at least one aperture of the footplate member is aligned with the second screw hole of the first end member, the at least one locking screw is insertible through the at least one aperture and into the second screw hole to attach the footplate member to the first end member in a second orientation relative to the first end member, the second orientation differing from the first orientation by said angle less than 180 degrees.

* * * * *